(12) United States Patent
Arnaut et al.

(10) Patent No.: US 8,173,872 B2
(45) Date of Patent: May 8, 2012

(54) BACILLUS THURINGIENSIS INSECTICIDAL PROTEINS

(75) Inventors: Greta Arnaut, Knessselare (BE); Annemie Boets, Velzeke (BE); Stijn Vanneste, Kortrijk (BE); Jeroen Van Rie, Eeklo (BE); Sara Van Houdt, Zottegem (BE)

(73) Assignee: Bayer CropScience NV, Diegem (BE)

( * ) Notice: Subject to any disclaimer, the term of this patent is extended or adjusted under 35 U.S.C. 154(b) by 0 days.

(21) Appl. No.: 12/888,815

(22) Filed: Sep. 23, 2010

(65) Prior Publication Data

US 2011/0041213 A1 Feb. 17, 2011

Related U.S. Application Data

(62) Division of application No. 11/783,379, filed on Apr. 9, 2007, now abandoned, which is a division of application No. 10/040,906, filed on Jan. 9, 2002, now Pat. No. 7,244,880.

(60) Provisional application No. 60/331,355, filed on Jan. 9, 2001.

(51) Int. Cl.
*A01H 5/00* (2006.01)
*C12N 15/82* (2006.01)
*C12N 15/32* (2006.01)
*C12N 1/21* (2006.01)

(52) U.S. Cl. .................. 800/302; 536/23.71; 424/93.2; 800/314

(58) Field of Classification Search ................. None
See application file for complete search history.

(56) References Cited

U.S. PATENT DOCUMENTS

| 5,073,632 | A  | 12/1991 | Donovan |
| 6,114,608 | A  | 9/2000  | Mettler et al. |
| 6,156,573 | A  | 12/2000 | Malvar et al. |
| 6,294,711 | B1 | 9/2001  | Meulewaeter et al. |
| 6,489,542 | B1 | 12/2002 | Corbin et al. |
| 6,593,293 | B1 | 7/2003  | Baum et al. |

FOREIGN PATENT DOCUMENTS

| WO | WO 98/40490 | 9/1998 |
| WO | WO 00/26371 | 5/2000 |
| WO | WO 01/19859 | 3/2001 |

OTHER PUBLICATIONS

Widner et al (1989, J. Bacteriol: 171:965-974).*
Audtho et al. (1999) Appl. Environ. Microbiol. 65(10):4601-4605.
Datla et al. (1997) Biotechnology Ann. Rev. 3:269-296.
Datta et al. (1990) Bio/Technology 8:736-740.
Kota et al. (1999) PNAS USA 96:1840-1845.
Krebbers et al. (1988) Plant Mol. Biol. 11:745-759.
Maqbool et al. (1998) XP-000881596 501-507.
Nicholls et al. (1989) J. Bacteriol. 171:5141-5147.
Schnepf et al. (1998) Microbiol. Mol. Biol. Rev. 62(3):775-806.
Wu et al. (1991) FEMS Microbiology Letters 81:31-36.
Widner and Whiteley (1989) Journal of Bacteriology 171:965-974.

* cited by examiner

*Primary Examiner* — Anne Kubelik
(74) *Attorney, Agent, or Firm* — Hunton & Williams LLP

(57) ABSTRACT

The invention pertains to novel insecticidal compounds derived from *Bacillus thuringiensis* strains. New proteins designated. Cry2Ae, Cry2Af, and Cry2Ag, and variants thereof are provided, as well as DNA sequences encoding these proteins or their variants. Further provided are recombinant hosts expressing such proteins, particularly plant cells and plants.

27 Claims, No Drawings

SEQUENCE LISTING

```
<160> NUMBER OF SEQ ID NOS: 9

<210> SEQ ID NO 1
<211> LENGTH: 1899
<212> TYPE: DNA
<213> ORGANISM: Bacillus thuringiensis
<220> FEATURE:
<221> NAME/KEY: CDS
<222> LOCATION: (1)..(1896)
<223> OTHER INFORMATION:

<400> SEQUENCE: 1 atg aat aat gta tta aat aac gga aga act act att tgt gat gcg tat        48
Met Asn Asn Val Leu Asn Asn Gly Arg Thr Thr Ile Cys Asp Ala Tyr
1               5                   10                  15 aat gta gtg gcc cat gat cca ttt agt ttt gag cat aaa tca tta gat        96
Asn Val Val Ala His Asp Pro Phe Ser Phe Glu His Lys Ser Leu Asp
            20                  25                  30 acc atc cga aaa gaa tgg atg gag tgg aaa aga aca gat cat agt tta       144
Thr Ile Arg Lys Glu Trp Met Glu Trp Lys Arg Thr Asp His Ser Leu
        35                  40                  45 tat gta gct cct ata gtc gga act gtt tct agc ttt ctg cta aag aag       192
Tyr Val Ala Pro Ile Val Gly Thr Val Ser Ser Phe Leu Leu Lys Lys
    50                  55                  60 gtg ggg agt ctt att gga aaa agg ata ttg agt gaa tta tgg ggg tta       240
Val Gly Ser Leu Ile Gly Lys Arg Ile Leu Ser Glu Leu Trp Gly Leu
65                  70                  75                  80 ata ttt cct agt ggt agc aca aat cta atg caa gat att tta agg gag       288
Ile Phe Pro Ser Gly Ser Thr Asn Leu Met Gln Asp Ile Leu Arg Glu
                85                  90                  95 aca gaa caa ttc cta aat caa aga ctt aat aca gac act ctt gcc cgt       336
Thr Glu Gln Phe Leu Asn Gln Arg Leu Asn Thr Asp Thr Leu Ala Arg
            100                 105                 110 gta aat gcg gaa ttg gaa ggg ctg caa gcg aat ata agg gag ttt aat       384
Val Asn Ala Glu Leu Glu Gly Leu Gln Ala Asn Ile Arg Glu Phe Asn
        115                 120                 125 caa caa gta gat aat ttt tta aat cct act caa aac cct gtt cct tta       432
Gln Gln Val Asp Asn Phe Leu Asn Pro Thr Gln Asn Pro Val Pro Leu
    130                 135                 140 tca ata act tct tca gtt aat aca atg cag caa tta ttt cta aat aga       480
Ser Ile Thr Ser Ser Val Asn Thr Met Gln Gln Leu Phe Leu Asn Arg
```

```
                   145                 150                 155                 160
tta ccc cag ttc cgt gtg caa gga tac caa ctg tta tta tta cct tta          528
Leu Pro Gln Phe Arg Val Gln Gly Tyr Gln Leu Leu Leu Leu Pro Leu
                165                 170                 175 ttt gca cag gca gcc aat atg cat ctt tct ttt att aga gat gtt gtt          576
Phe Ala Gln Ala Ala Asn Met His Leu Ser Phe Ile Arg Asp Val Val
            180                 185                 190 ctc aat gca gat gaa tgg gga att tca gca gca aca tta cgt acg tat          624
Leu Asn Ala Asp Glu Trp Gly Ile Ser Ala Ala Thr Leu Arg Thr Tyr
        195                 200                 205 caa aat tat ctg aaa aat tat aca aca gag tac tct aat tat tgt ata          672
Gln Asn Tyr Leu Lys Asn Tyr Thr Thr Glu Tyr Ser Asn Tyr Cys Ile
    210                 215                 220 aat acg tat caa act gcg ttt aga ggt tta aac acc cgt tta cac gat          720
Asn Thr Tyr Gln Thr Ala Phe Arg Gly Leu Asn Thr Arg Leu His Asp
225                 230                 235                 240 atg tta gaa ttt aga aca tat atg ttt tta aat gta ttt gaa tat gta          768
Met Leu Glu Phe Arg Thr Tyr Met Phe Leu Asn Val Phe Glu Tyr Val
                245                 250                 255 tct atc tgg tcg ttg ttt aaa tat caa agc ctt cta gta tct tct ggc          816
Ser Ile Trp Ser Leu Phe Lys Tyr Gln Ser Leu Leu Val Ser Ser Gly
            260                 265                 270 gct aat tta tat gca agc ggt agt gga cca cag cag act caa tca ttt          864
Ala Asn Leu Tyr Ala Ser Gly Ser Gly Pro Gln Gln Thr Gln Ser Phe
        275                 280                 285 act tca caa gac tgg cca ttt tta tat tct ctt ttc caa gtt aat tca          912
Thr Ser Gln Asp Trp Pro Phe Leu Tyr Ser Leu Phe Gln Val Asn Ser
    290                 295                 300 aat tat gtg tta aat ggc ttt agt ggc gct aga ctt acg cag act ttc          960
Asn Tyr Val Leu Asn Gly Phe Ser Gly Ala Arg Leu Thr Gln Thr Phe
305                 310                 315                 320 cct aat att ggt ggt tta cct ggt act act aca act cac gca ttg ctt         1008
Pro Asn Ile Gly Gly Leu Pro Gly Thr Thr Thr Thr His Ala Leu Leu
                325                 330                 335 gcg gca agg gtc aat tac agt gga gga gtt tcg tct ggt gat ata ggc         1056
Ala Ala Arg Val Asn Tyr Ser Gly Gly Val Ser Ser Gly Asp Ile Gly
            340                 345                 350 gct gtg ttt aat caa aat ttt agt tgt agc aca ttt ctc cca cct ttg         1104
Ala Val Phe Asn Gln Asn Phe Ser Cys Ser Thr Phe Leu Pro Pro Leu
        355                 360                 365 tta aca cca ttt gtt agg agt tgg cta gat tca ggt tca gat cga ggg         1152
Leu Thr Pro Phe Val Arg Ser Trp Leu Asp Ser Gly Ser Asp Arg Gly
    370                 375                 380 ggt gtt aat acc gtt aca aat tgg caa aca gaa tcg ttt gag tca act         1200
Gly Val Asn Thr Val Thr Asn Trp Gln Thr Glu Ser Phe Glu Ser Thr
385                 390                 395                 400 tta ggt tta agg tgt ggt gct ttt aca gct cgt ggt aat tca aac tat         1248
Leu Gly Leu Arg Cys Gly Ala Phe Thr Ala Arg Gly Asn Ser Asn Tyr
                405                 410                 415 ttc cca gat tat ttt atc cgt aat att tca gga gtt cct tta gtt gtt         1296
Phe Pro Asp Tyr Phe Ile Arg Asn Ile Ser Gly Val Pro Leu Val Val
            420                 425                 430 aga aat gaa gat tta aga aga ccg tta cac tat aat gaa ata aga aat         1344
Arg Asn Glu Asp Leu Arg Arg Pro Leu His Tyr Asn Glu Ile Arg Asn
        435                 440                 445 ata gaa agt cct tca gga aca cct ggt gga tta cga gct tat atg gta         1392
Ile Glu Ser Pro Ser Gly Thr Pro Gly Gly Leu Arg Ala Tyr Met Val
    450                 455                 460 tct gtg cat aat aga aaa aat aat atc tat gcc gtg cat gaa aat ggt         1440
Ser Val His Asn Arg Lys Asn Asn Ile Tyr Ala Val His Glu Asn Gly
```

```
            465                 470                 475                 480
act atg att cat tta gcg ccg gaa gat tat aca gga ttc acc ata tcg       1488
Thr Met Ile His Leu Ala Pro Glu Asp Tyr Thr Gly Phe Thr Ile Ser
                    485                 490                 495 ccg ata cat gca act caa gtg aat aat caa acg cga aca ttt att tct       1536
Pro Ile His Ala Thr Gln Val Asn Asn Gln Thr Arg Thr Phe Ile Ser
                500                 505                 510 gaa aaa ttt gga aat caa ggt gat tcc tta aga ttt gaa caa agc aac       1584
Glu Lys Phe Gly Asn Gln Gly Asp Ser Leu Arg Phe Glu Gln Ser Asn
            515                 520                 525 acg aca gca cgt tat aca ctt aga gga aat gga aat agt tac aat ctt       1632
Thr Thr Ala Arg Tyr Thr Leu Arg Gly Asn Gly Asn Ser Tyr Asn Leu
        530                 535                 540 tat tta aga gta tct tca cta gga aat tcc act att cga gtt act ata       1680
Tyr Leu Arg Val Ser Ser Leu Gly Asn Ser Thr Ile Arg Val Thr Ile
545                 550                 555                 560 aac ggt agg gtt tat act gct tca aat gtt aat act act aca aat aac       1728
Asn Gly Arg Val Tyr Thr Ala Ser Asn Val Asn Thr Thr Thr Asn Asn
                565                 570                 575 gat gga gtt aat gat aat ggc gct cgt ttt tta gat att aat atg ggt       1776
Asp Gly Val Asn Asp Asn Gly Ala Arg Phe Leu Asp Ile Asn Met Gly
            580                 585                 590 aat gta gta gca agt gat aat act aat gta ccg tta gat ata aat gtg       1824
Asn Val Val Ala Ser Asp Asn Thr Asn Val Pro Leu Asp Ile Asn Val
        595                 600                 605 aca ttt aac tcc ggt act caa ttt gag ctt atg aat att atg ttt gtt       1872
Thr Phe Asn Ser Gly Thr Gln Phe Glu Leu Met Asn Ile Met Phe Val
    610                 615                 620 cca act aat ctt cca cca ata tat taa                                   1899
Pro Thr Asn Leu Pro Pro Ile Tyr
625                 630

<210> SEQ ID NO 2
<211> LENGTH: 632
<212> TYPE: PRT
<213> ORGANISM: Bacillus thuringiensis

<400> SEQUENCE: 2

Met Asn Asn Val Leu Asn Asn Gly Arg Thr Thr Ile Cys Asp Ala Tyr
1               5                   10                  15

Asn Val Val Ala His Asp Pro Phe Ser Phe Glu His Lys Ser Leu Asp
                20                  25                  30

Thr Ile Arg Lys Glu Trp Met Glu Trp Lys Arg Thr Asp His Ser Leu
            35                  40                  45

Tyr Val Ala Pro Ile Val Gly Thr Val Ser Ser Phe Leu Leu Lys Lys
        50                  55                  60

Val Gly Ser Leu Ile Gly Lys Arg Ile Leu Ser Glu Leu Trp Gly Leu
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Ala Arg
            100                 105                 110

Val Asn Ala Glu Leu Glu Gly Leu Gln Ala Asn Ile Arg Glu Phe Asn
        115                 120                 125

Gln Gln Val Asp Asn Phe Leu Asn Pro Thr Gln Asn Pro Val Pro Leu
    130                 135                 140

Ser Ile Thr Ser Ser Val Asn Thr Met Gln Gln Leu Phe Leu Asn Arg
145                 150                 155                 160
```

```
Leu Pro Gln Phe Arg Val Gln Gly Tyr Gln Leu Leu Leu Pro Leu
                165                 170                 175

Phe Ala Gln Ala Ala Asn Met His Leu Ser Phe Ile Arg Asp Val Val
            180                 185                 190

Leu Asn Ala Asp Glu Trp Gly Ile Ser Ala Ala Thr Leu Arg Thr Tyr
        195                 200                 205

Gln Asn Tyr Leu Lys Asn Tyr Thr Thr Glu Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
            245                 250                 255

Ser Ile Trp Ser Leu Phe Lys Tyr Gln Ser Leu Leu Val Ser Ser Gly
        260                 265                 270

Ala Asn Leu Tyr Ala Ser Gly Ser Gly Pro Gln Gln Thr Gln Ser Phe
    275                 280                 285

Thr Ser Gln Asp Trp Pro Phe Leu Tyr Ser Leu Phe Gln Val Asn Ser
290                 295                 300

Asn Tyr Val Leu Asn Gly Phe Ser Gly Ala Arg Leu Thr Gln Thr Phe
305                 310                 315                 320

Pro Asn Ile Gly Gly Leu Pro Gly Thr Thr Thr His Ala Leu Leu
            325                 330                 335

Ala Ala Arg Val Asn Tyr Ser Gly Gly Val Ser Ser Gly Asp Ile Gly
            340                 345                 350

Ala Val Phe Asn Gln Asn Phe Ser Cys Ser Thr Phe Leu Pro Pro Leu
        355                 360                 365

Leu Thr Pro Phe Val Arg Ser Trp Leu Asp Ser Gly Ser Asp Arg Gly
    370                 375                 380

Gly Val Asn Thr Val Thr Asn Trp Gln Thr Glu Ser Phe Glu Ser Thr
385                 390                 395                 400

Leu Gly Leu Arg Cys Gly Ala Phe Thr Ala Arg Gly Asn Ser Asn Tyr
            405                 410                 415

Phe Pro Asp Tyr Phe Ile Arg Asn Ile Ser Gly Val Pro Leu Val Val
        420                 425                 430

Arg Asn Glu Asp Leu Arg Arg Pro Leu His Tyr Asn Glu Ile Arg Asn
    435                 440                 445

Ile Glu Ser Pro Ser Gly Thr Pro Gly Gly Leu Arg Ala Tyr Met Val
    450                 455                 460

Ser Val His Asn Arg Lys Asn Asn Ile Tyr Ala Val His Glu Asn Gly
465                 470                 475                 480

Thr Met Ile His Leu Ala Pro Glu Asp Tyr Thr Gly Phe Thr Ile Ser
            485                 490                 495

Pro Ile His Ala Thr Gln Val Asn Asn Gln Thr Arg Thr Phe Ile Ser
        500                 505                 510

Glu Lys Phe Gly Asn Gln Gly Asp Ser Leu Arg Phe Glu Gln Ser Asn
    515                 520                 525

Thr Thr Ala Arg Tyr Thr Leu Arg Gly Asn Gly Asn Ser Tyr Asn Leu
    530                 535                 540

Tyr Leu Arg Val Ser Ser Leu Gly Asn Ser Thr Ile Arg Val Thr Ile
545                 550                 555                 560

Asn Gly Arg Val Tyr Thr Ala Ser Asn Val Asn Thr Thr Asn Asn
            565                 570                 575

Asp Gly Val Asn Asp Asn Gly Ala Arg Phe Leu Asp Ile Asn Met Gly
        580                 585                 590
```

```
Asn Val Val Ala Ser Asp Asn Thr Asn Val Pro Leu Asp Ile Asn Val
            595                 600                 605

Thr Phe Asn Ser Gly Thr Gln Phe Glu Leu Met Asn Ile Met Phe Val
            610                 615                 620

Pro Thr Asn Leu Pro Pro Ile Tyr
625                 630

<210> SEQ ID NO 3
<211> LENGTH: 1899
<212> TYPE: DNA
<213> ORGANISM: Bacillus thuringiensis
<220> FEATURE:
<221> NAME/KEY: CDS
<222> LOCATION: (1)..(1896)
<223> OTHER INFORMATION:

<400> SEQUENCE: 3 atg aat agt gta ttg aat agc gga aga act act att tgt gat gcg tat      48
Met Asn Ser Val Leu Asn Ser Gly Arg Thr Thr Ile Cys Asp Ala Tyr
1               5                   10                  15 aat gta gtg gct cat gat cca ttt agt ttt caa cat aaa tca tta gat      96
Asn Val Val Ala His Asp Pro Phe Ser Phe Gln His Lys Ser Leu Asp
                20                  25                  30 acc ata caa gaa gaa tgg atg gag tgg aaa aaa gat aat cat agt tta     144
Thr Ile Gln Glu Glu Trp Met Glu Trp Lys Lys Asp Asn His Ser Leu
            35                  40                  45 tat gta gat cct att gtt gga act gtg gct agt ttt ctt tta aag aaa     192
Tyr Val Asp Pro Ile Val Gly Thr Val Ala Ser Phe Leu Leu Lys Lys
        50                  55                  60 gtg ggg agt ctt gtt gga aaa aga ata ctg agt gag tta cgg aat tta     240
Val Gly Ser Leu Val Gly Lys Arg Ile Leu Ser Glu Leu Arg Asn Leu
65                  70                  75                  80 ata ttt cct agt ggc agt aca aat cta atg caa gat att tta aga gag     288
Ile Phe Pro Ser Gly Ser Thr Asn Leu Met Gln Asp Ile Leu Arg Glu
                85                  90                  95 aca gaa aaa ttc ctg aat caa aga ctt aat aca gac act ctt gcc cgt     336
Thr Glu Lys Phe Leu Asn Gln Arg Leu Asn Thr Asp Thr Leu Ala Arg
            100                 105                 110 gta aat gcg gaa ttg aca ggg ctg caa gca aat gta gaa gag ttt aat     384
Val Asn Ala Glu Leu Thr Gly Leu Gln Ala Asn Val Glu Glu Phe Asn
        115                 120                 125 cga caa gta gat aat ttt ttg aac cct aac cga aat gct gtt cct tta     432
Arg Gln Val Asp Asn Phe Leu Asn Pro Asn Arg Asn Ala Val Pro Leu
    130                 135                 140 tca ata act tct tca gtt aat aca atg cag caa tta ttt cta aat aga     480
Ser Ile Thr Ser Ser Val Asn Thr Met Gln Gln Leu Phe Leu Asn Arg
145                 150                 155                 160 tta acc cag ttc cag atg caa gga tac caa ttg tta tta cct tta         528
Leu Thr Gln Phe Gln Met Gln Gly Tyr Gln Leu Leu Leu Pro Leu
                165                 170                 175 ttt gca cag gca gcc aat tta cat ctt tct ttt att aga gat gtt att     576
Phe Ala Gln Ala Ala Asn Leu His Leu Ser Phe Ile Arg Asp Val Ile
            180                 185                 190 ctt aat gca gac gaa tgg gga att tca gca gca aca tta cgt acg tat     624
Leu Asn Ala Asp Glu Trp Gly Ile Ser Ala Ala Thr Leu Arg Thr Tyr
        195                 200                 205 caa aat cac ctg aga aat tat aca aga gat tac tct aat tat tgt ata     672
Gln Asn His Leu Arg Asn Tyr Thr Arg Asp Tyr Ser Asn Tyr Cys Ile
    210                 215                 220 aat acg tat caa act gcg ttt aga ggt tta aac acc cgt tta cac gat     720
Asn Thr Tyr Gln Thr Ala Phe Arg Gly Leu Asn Thr Arg Leu His Asp
225                 230                 235                 240
```

```
                 225                     230                     235                     240
atg tta gaa ttt aga aca tat atg ttt tta aat gta ttt gag tat gta     768
Met Leu Glu Phe Arg Thr Tyr Met Phe Leu Asn Val Phe Glu Tyr Val
                245                     250                     255 tct atc tgg tcg ttg ttt aaa tat caa agc ctt cta gtc tct tct ggc     816
Ser Ile Trp Ser Leu Phe Lys Tyr Gln Ser Leu Leu Val Ser Ser Gly
        260                     265                     270 gct aat tta tat gca agt ggt agt gga cca cag cag acc caa tca ttt     864
Ala Asn Leu Tyr Ala Ser Gly Ser Gly Pro Gln Gln Thr Gln Ser Phe
            275                     280                     285 act tca caa gac tgg cca ttt tta tat tct ctt ttc caa gtt aat tca     912
Thr Ser Gln Asp Trp Pro Phe Leu Tyr Ser Leu Phe Gln Val Asn Ser
    290                     295                     300 aat tat gtg tta aat ggc ttt agt ggc gct aga ctt acg cag act ttc     960
Asn Tyr Val Leu Asn Gly Phe Ser Gly Ala Arg Leu Thr Gln Thr Phe
305                     310                     315                     320 cct aat att gtt ggt tta cct ggt act act aca act cac gca ttg ctt    1008
Pro Asn Ile Val Gly Leu Pro Gly Thr Thr Thr Thr His Ala Leu Leu
                325                     330                     335 gct gca agg gtc aat tac agt gga gga gtt tcg tct ggt gat ata ggc    1056
Ala Ala Arg Val Asn Tyr Ser Gly Gly Val Ser Ser Gly Asp Ile Gly
        340                     345                     350 gct gtg ttt aat caa aat ttt agt tgt agc aca ttt ctc cca cct ttg    1104
Ala Val Phe Asn Gln Asn Phe Ser Cys Ser Thr Phe Leu Pro Pro Leu
            355                     360                     365 tta aca cca ttt gtt agg agt tgg cta gat tca ggt tca gat cgg ggg    1152
Leu Thr Pro Phe Val Arg Ser Trp Leu Asp Ser Gly Ser Asp Arg Gly
    370                     375                     380 ggg atc aat acc gtt acc aat tgg caa aca gaa tcc ttt gag aca act    1200
Gly Ile Asn Thr Val Thr Asn Trp Gln Thr Glu Ser Phe Glu Thr Thr
385                     390                     395                     400 tta ggt tta agg agt ggt gct ttt aca gct cga ggt aat tca aac tat    1248
Leu Gly Leu Arg Ser Gly Ala Phe Thr Ala Arg Gly Asn Ser Asn Tyr
                405                     410                     415 ttc cca gat tat ttt atc cgt aat att tcc gga gtt cct tta gtt gtt    1296
Phe Pro Asp Tyr Phe Ile Arg Asn Ile Ser Gly Val Pro Leu Val Val
        420                     425                     430 aga aat gaa gat tta aga aga ccg tta cac tat aat caa ata aga aat    1344
Arg Asn Glu Asp Leu Arg Arg Pro Leu His Tyr Asn Gln Ile Arg Asn
            435                     440                     445 ata gaa agt cct tca gga aca cct ggt gga tta cga gct tat atg gta    1392
Ile Glu Ser Pro Ser Gly Thr Pro Gly Gly Leu Arg Ala Tyr Met Val
    450                     455                     460 tct gtg cat aac aga aaa aat aat atc tat gcc gtt cat gaa aat ggt    1440
Ser Val His Asn Arg Lys Asn Asn Ile Tyr Ala Val His Glu Asn Gly
465                     470                     475                     480 act atg att cat tta gcg ccg gaa gat tat aca gga ttt act ata tcg    1488
Thr Met Ile His Leu Ala Pro Glu Asp Tyr Thr Gly Phe Thr Ile Ser
                485                     490                     495 ccg ata cat gca act caa gtg aat aat caa acg cga aca ttt att tct    1536
Pro Ile His Ala Thr Gln Val Asn Asn Gln Thr Arg Thr Phe Ile Ser
        500                     505                     510 gaa aaa ttt gga aat caa ggt gat tcc tta aga ttt gaa caa agc aac    1584
Glu Lys Phe Gly Asn Gln Gly Asp Ser Leu Arg Phe Glu Gln Ser Asn
            515                     520                     525 acg aca gct cgt tat aca ctt aga ggg aat gga aat agt tac aat ctt    1632
Thr Thr Ala Arg Tyr Thr Leu Arg Gly Asn Gly Asn Ser Tyr Asn Leu
    530                     535                     540 tat tta aga gta tct tca ata gga aat tcc act att cga gtt act ata    1680
Tyr Leu Arg Val Ser Ser Ile Gly Asn Ser Thr Ile Arg Val Thr Ile
```

```
                    545                 550                 555                 560
aac ggt aga gtt tat act gct tca aat gtt aat act act aca aat aac        1728
Asn Gly Arg Val Tyr Thr Ala Ser Asn Val Asn Thr Thr Thr Asn Asn
            565                 570                 575 gat gga gtt aat gat aat gga gct cgt ttt tca gat att aat att ggt        1776
Asp Gly Val Asn Asp Asn Gly Ala Arg Phe Ser Asp Ile Asn Ile Gly
            580                 585                 590 aat gta gta gca agt gat aat act aat gta ccg tta gat ata aac gtg        1824
Asn Val Val Ala Ser Asp Asn Thr Asn Val Pro Leu Asp Ile Asn Val
            595                 600                 605 aca tta aat tct ggt act caa ttt gag ctt atg aat att atg ttt gtt        1872
Thr Leu Asn Ser Gly Thr Gln Phe Glu Leu Met Asn Ile Met Phe Val
            610                 615                 620 cca act aat atc tca cca ctt tat taa                                    1899
Pro Thr Asn Ile Ser Pro Leu Tyr
625                 630

<210> SEQ ID NO 4
<211> LENGTH: 632
<212> TYPE: PRT
<213> ORGANISM: Bacillus thuringiensis

<400> SEQUENCE: 4

Met Asn Ser Val Leu Asn Ser Gly Arg Thr Thr Ile Cys Asp Ala Tyr
1               5                   10                  15

Asn Val Val Ala His Asp Pro Phe Ser Phe Gln His Lys Ser Leu Asp
                20                  25                  30

Thr Ile Gln Glu Glu Trp Met Glu Trp Lys Lys Asp Asn His Ser Leu
            35                  40                  45

Tyr Val Asp Pro Ile Val Gly Thr Val Ala Ser Phe Leu Leu Lys Lys
        50                  55                  60

Val Gly Ser Leu Val Gly Lys Arg Ile Leu Ser Glu Leu Arg Asn Leu
65                  70                  75                  80

Ile Phe Pro Ser Gly Ser Thr Asn Leu Met Gln Asp Ile Leu Arg Glu
                85                  90                  95

Thr Glu Lys Phe Leu Asn Gln Arg Leu Asn Thr Asp Thr Leu Ala Arg
            100                 105                 110

Val Asn Ala Glu Leu Thr Gly Leu Gln Ala Asn Val Glu Glu Phe Asn
        115                 120                 125

Arg Gln Val Asp Asn Phe Leu Asn Pro Asn Arg Asn Ala Val Pro Leu
130                 135                 140

Ser Ile Thr Ser Ser Val Asn Thr Met Gln Gln Leu Phe Leu Asn Arg
145                 150                 155                 160

Leu Thr Gln Phe Gln Met Gln Gly Tyr Gln Leu Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Asp Glu Trp Gly Ile Ser Ala Ala Thr Leu Arg Thr Tyr
        195                 200                 205

Gln Asn His Leu Arg Asn Tyr Thr Arg Asp Tyr Ser Asn Tyr Cys Ile
210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270
```

```
Ala Asn Leu Tyr Ala Ser Gly Ser Gly Pro Gln Gln Thr Gln Ser Phe
        275                 280                 285

Thr Ser Gln Asp Trp Pro Phe Leu Tyr Ser Leu Phe Gln Val Asn Ser
    290                 295                 300

Asn Tyr Val Leu Asn Gly Phe Ser Gly Ala Arg Leu Thr Gln Thr Phe
305                 310                 315                 320

Pro Asn Ile Val Gly Leu Pro Gly Thr Thr Thr His Ala Leu Leu
                325                 330                 335

Ala Ala Arg Val Asn Tyr Ser Gly Gly Val Ser Ser Gly Asp Ile Gly
            340                 345                 350

Ala Val Phe Asn Gln Asn Phe Ser Cys Ser Thr Phe Leu Pro Pro Leu
        355                 360                 365

Leu Thr Pro Phe Val Arg Ser Trp Leu Asp Ser Gly Ser Asp Arg Gly
    370                 375                 380

Gly Ile Asn Thr Val Thr Asn Trp Gln Thr Glu Ser Phe Glu Thr Thr
385                 390                 395                 400

Leu Gly Leu Arg Ser Gly Ala Phe Thr Ala Arg Gly Asn Ser Asn Tyr
                405                 410                 415

Phe Pro Asp Tyr Phe Ile Arg Asn Ile Ser Gly Val Pro Leu Val Val
            420                 425                 430

Arg Asn Glu Asp Leu Arg Arg Pro Leu His Tyr Asn Gln Ile Arg Asn
        435                 440                 445

Ile Glu Ser Pro Ser Gly Thr Pro Gly Gly Leu Arg Ala Tyr Met Val
    450                 455                 460

Ser Val His Asn Arg Lys Asn Asn Ile Tyr Ala Val His Glu Asn Gly
465                 470                 475                 480

Thr Met Ile His Leu Ala Pro Glu Asp Tyr Thr Gly Phe Thr Ile Ser
                485                 490                 495

Pro Ile His Ala Thr Gln Val Asn Asn Gln Thr Arg Thr Phe Ile Ser
            500                 505                 510

Glu Lys Phe Gly Asn Gln Gly Asp Ser Leu Arg Phe Glu Gln Ser Asn
        515                 520                 525

Thr Thr Ala Arg Tyr Thr Leu Arg Gly Asn Gly Asn Ser Tyr Asn Leu
    530                 535                 540

Tyr Leu Arg Val Ser Ser Ile Gly Asn Ser Thr Ile Arg Val Thr Ile
545                 550                 555                 560

Asn Gly Arg Val Tyr Thr Ala Ser Asn Val Asn Thr Thr Asn Asn
                565                 570                 575

Asp Gly Val Asn Asp Asn Gly Ala Arg Phe Ser Asp Ile Asn Ile Gly
            580                 585                 590

Asn Val Val Ala Ser Asp Asn Thr Asn Val Pro Leu Asp Ile Asn Val
        595                 600                 605

Thr Leu Asn Ser Gly Thr Gln Phe Glu Leu Met Asn Ile Met Phe Val
    610                 615                 620

Pro Thr Asn Ile Ser Pro Leu Tyr
625                 630

<210> SEQ ID NO 5
<211> LENGTH: 1884
<212> TYPE: DNA
<213> ORGANISM: Bacillus thuringiensis
<220> FEATURE:
<221> NAME/KEY: CDS
<222> LOCATION: (1)..(1881)
<223> OTHER INFORMATION:
```

<400> SEQUENCE: 5

```
atg aat aat gta ttg aat agc gaa aga act act aag tgt ggt gcg tat      48
Met Asn Asn Val Leu Asn Ser Glu Arg Thr Thr Lys Cys Gly Ala Tyr
 1               5                  10                  15 aac gta gtg gct cat gat cca ttc agt ttt gaa cat aaa tca tta gat      96
Asn Val Val Ala His Asp Pro Phe Ser Phe Glu His Lys Ser Leu Asp
                20                  25                  30 acc ata caa aaa gaa tgg atg gag tgg aaa aga act gat cat agt tta     144
Thr Ile Gln Lys Glu Trp Met Glu Trp Lys Arg Thr Asp His Ser Leu
            35                  40                  45 tat gta tct cct att gta gga act ata gcc agt ttt ctg tta aag aaa     192
Tyr Val Ser Pro Ile Val Gly Thr Ile Ala Ser Phe Leu Leu Lys Lys
        50                  55                  60 ata gga ggg ctt ata gga aaa aga ata tta agt gag tta aag aat tta     240
Ile Gly Gly Leu Ile Gly Lys Arg Ile Leu Ser Glu Leu Lys Asn Leu
 65                  70                  75                  80 att ttt cct agt ggt agt ata gaa tca atg caa gat att tta aga ggg     288
Ile Phe Pro Ser Gly Ser Ile Glu Ser Met Gln Asp Ile Leu Arg Gly
                85                  90                  95 gca gaa caa ttt cta aat caa aga ctt gat gca gac acc ttt agt cgt     336
Ala Glu Gln Phe Leu Asn Gln Arg Leu Asp Ala Asp Thr Phe Ser Arg
                100                 105                 110 gta gaa gca gaa ttg aga ggg ctt caa gca aat gta gag gaa ttt aat     384
Val Glu Ala Glu Leu Arg Gly Leu Gln Ala Asn Val Glu Glu Phe Asn
            115                 120                 125 cga caa gtg gac aat ttt tta aac cca aat caa aac cct gcc cct tta     432
Arg Gln Val Asp Asn Phe Leu Asn Pro Asn Gln Asn Pro Ala Pro Leu
        130                 135                 140 gca ata att gat tcg gtt aat aca ttg caa caa tta ttc cta agt aga     480
Ala Ile Ile Asp Ser Val Asn Thr Leu Gln Gln Leu Phe Leu Ser Arg
145                 150                 155                 160 tta ccc cag ttc cag ata caa cgc tat cag cta tta tta cct tta         528
Leu Pro Gln Phe Gln Ile Gln Arg Tyr Gln Leu Leu Leu Pro Leu
                165                 170                 175 ttt gca caa gca gcc aat tta cac ctt tct ttt att aga gac gtt att     576
Phe Ala Gln Ala Ala Asn Leu His Leu Ser Phe Ile Arg Asp Val Ile
                180                 185                 190 ctt aat gca gat gaa tgg gga ata cca gct gca acg gtg cgc aca tat     624
Leu Asn Ala Asp Glu Trp Gly Ile Pro Ala Ala Thr Val Arg Thr Tyr
            195                 200                 205 aga gag cac cta caa aga tat aca cgc gaa tac tcc aat tat tgt ata     672
Arg Glu His Leu Gln Arg Tyr Thr Arg Glu Tyr Ser Asn Tyr Cys Ile
        210                 215                 220 aat acg tat caa act gcg ttt aga ggg tta aat gcc act tta cac gat     720
Asn Thr Tyr Gln Thr Ala Phe Arg Gly Leu Asn Ala Thr Leu His Asp
225                 230                 235                 240 ttt cta gaa ttt aga aca tat atg ttt tta aat gta tta gac tat gta     768
Phe Leu Glu Phe Arg Thr Tyr Met Phe Leu Asn Val Leu Asp Tyr Val
                245                 250                 255 tct atc tgg tcg ttg ttt aaa tat cag agc ctt ctg gta tcc tct ggc     816
Ser Ile Trp Ser Leu Phe Lys Tyr Gln Ser Leu Leu Val Ser Ser Gly
                260                 265                 270 gct aat tta tat gcg agt ggt agt gga gta aca aat aga caa tca ttt     864
Ala Asn Leu Tyr Ala Ser Gly Ser Gly Val Thr Asn Arg Gln Ser Phe
            275                 280                 285 act gca caa gac tgg cca ttt tta aat tct ctt ttc caa gtt aat caa     912
Thr Ala Gln Asp Trp Pro Phe Leu Asn Ser Leu Phe Gln Val Asn Gln
        290                 295                 300 aat tat gta tta aca ggt atg aat ggt tat agg tat act tta agt tct     960
Asn Tyr Val Leu Thr Gly Met Asn Gly Tyr Arg Tyr Thr Leu Ser Ser
```

```
                305                 310                 315                 320
gtt ttt ggt aca aat caa aca ata cat tct gtt agg agt aat tat agg      1008
Val Phe Gly Thr Asn Gln Thr Ile His Ser Val Arg Ser Asn Tyr Arg
                325                 330                 335 ggc ggg gtt tca tct ggt tac att gga gtt aat ctt agt gaa ggt gac      1056
Gly Gly Val Ser Ser Gly Tyr Ile Gly Val Asn Leu Ser Glu Gly Asp
                340                 345                 350 caa aat ttt agt tgt agt aca ttt ttg gat cct tta gaa aca ccg ttt      1104
Gln Asn Phe Ser Cys Ser Thr Phe Leu Asp Pro Leu Glu Thr Pro Phe
                355                 360                 365 att aga agt tgg ctg gat tca ggt agc gat gat ggc ttt aat tgg agt      1152
Ile Arg Ser Trp Leu Asp Ser Gly Ser Asp Asp Gly Phe Asn Trp Ser
            370                 375                 380 aca gga gtc ttt aca aca act att ggt tta cct act tgt agc att ttt      1200
Thr Gly Val Phe Thr Thr Thr Ile Gly Leu Pro Thr Cys Ser Ile Phe
385                 390                 395                 400 tgg cct cgt ggt aac tcg aac tat ttt cca gat tat ttt ata cga aat      1248
Trp Pro Arg Gly Asn Ser Asn Tyr Phe Pro Asp Tyr Phe Ile Arg Asn
                405                 410                 415 att tct ggt gtc gtt ggt cgt ctt agg aac gaa gat tta aga aga cca      1296
Ile Ser Gly Val Val Gly Arg Leu Arg Asn Glu Asp Leu Arg Arg Pro
                420                 425                 430 cta tat ttt aat gag ata aga aat ata gta gga aat aac aat cca ccg      1344
Leu Tyr Phe Asn Glu Ile Arg Asn Ile Val Gly Asn Asn Asn Pro Pro
            435                 440                 445 gca act gga tcg tta tca gtc gcc agc cta gtc tct gtg cat aac aga      1392
Ala Thr Gly Ser Leu Ser Val Ala Ser Leu Val Ser Val His Asn Arg
450                 455                 460 aaa aat aat att tat gct gct cat gaa aat ggt act atg att cat ttg      1440
Lys Asn Asn Ile Tyr Ala Ala His Glu Asn Gly Thr Met Ile His Leu
465                 470                 475                 480 gca ccg gaa gat tat aca ggt ttc aca atg tca cca ata cat gca act      1488
Ala Pro Glu Asp Tyr Thr Gly Phe Thr Met Ser Pro Ile His Ala Thr
                485                 490                 495 caa gta aat aat caa aca cga aca ttt att tcc gag aaa tta gga aac      1536
Gln Val Asn Asn Gln Thr Arg Thr Phe Ile Ser Glu Lys Leu Gly Asn
                500                 505                 510 caa ggt gat tcc ttg aga ttt gaa caa aca aat aca acg gct cga tac      1584
Gln Gly Asp Ser Leu Arg Phe Glu Gln Thr Asn Thr Thr Ala Arg Tyr
            515                 520                 525 aca ttt aga ggg aat gga aat agt tac aat ctt tat tta aga gta tct      1632
Thr Phe Arg Gly Asn Gly Asn Ser Tyr Asn Leu Tyr Leu Arg Val Ser
530                 535                 540 tca cta gga aat tcc aca att cga gtt act ata aac ggt aga gtt tat      1680
Ser Leu Gly Asn Ser Thr Ile Arg Val Thr Ile Asn Gly Arg Val Tyr
545                 550                 555                 560 act gtt tca aac gtc aat act act aca aat aac gat gga gtt gtt gat      1728
Thr Val Ser Asn Val Asn Thr Thr Thr Asn Asn Asp Gly Val Val Asp
                565                 570                 575 aat ggc gct cgt ttt tca gat att aat ata ggt aat gta gtg gca agt      1776
Asn Gly Ala Arg Phe Ser Asp Ile Asn Ile Gly Asn Val Val Ala Ser
                580                 585                 590 gct aat act aat ata cca tta gat ata aat gta aca ttt aac tct ggt      1824
Ala Asn Thr Asn Ile Pro Leu Asp Ile Asn Val Thr Phe Asn Ser Gly
            595                 600                 605 acg caa ttt gag ctt atg aat att atg ttt gtt cca act aat att cca      1872
Thr Gln Phe Glu Leu Met Asn Ile Met Phe Val Pro Thr Asn Ile Pro
610                 615                 620 cca att tat taa                                                      1884
Pro Ile Tyr
```

<210> SEQ ID NO 6
<211> LENGTH: 627
<212> TYPE: PRT
<213> ORGANISM: Bacillus thuringiensis

<400> SEQUENCE: 6

| |

```
                    370                375                380
Thr Gly Val Phe Thr Thr Ile Gly Leu Pro Thr Cys Ser Ile Phe
385                 390                395                400

Trp Pro Arg Gly Asn Ser Asn Tyr Phe Pro Asp Tyr Phe Ile Arg Asn
                405                410                415

Ile Ser Gly Val Val Gly Arg Leu Arg Asn Glu Asp Leu Arg Arg Pro
                420                425                430

Leu Tyr Phe Asn Glu Ile Arg Asn Ile Val Gly Asn Asn Pro Pro
            435                440                445

Ala Thr Gly Ser Leu Ser Val Ala Ser Leu Val Ser Val His Asn Arg
450                455                460

Lys Asn Asn Ile Tyr Ala Ala His Glu Asn Gly Thr Met Ile His Leu
465             470                475                480

Ala Pro Glu Asp Tyr Thr Gly Phe Thr Met Ser Pro Ile His Ala Thr
                    485                490                495

Gln Val Asn Asn Gln Thr Arg Thr Phe Ile Ser Glu Lys Leu Gly Asn
                500                505                510

Gln Gly Asp Ser Leu Arg Phe Glu Gln Thr Asn Thr Thr Ala Arg Tyr
            515                520                525

Thr Phe Arg Gly Asn Gly Asn Ser Tyr Asn Leu Tyr Leu Arg Val Ser
    530                535                540

Ser Leu Gly Asn Ser Thr Ile Arg Val Thr Ile Asn Gly Arg Val Tyr
545                550                555                560

Thr Val Ser Asn Val Asn Thr Thr Thr Asn Asn Asp Gly Val Val Asp
                565                570                575

Asn Gly Ala Arg Phe Ser Asp Ile Asn Ile Gly Asn Val Val Ala Ser
                580                585                590

Ala Asn Thr Asn Ile Pro Leu Asp Ile Asn Val Thr Phe Asn Ser Gly
        595                600                605

Thr Gln Phe Glu Leu Met Asn Ile Met Phe Val Pro Thr Asn Ile Pro
    610                615                620

Pro Ile Tyr
625

<210> SEQ ID NO 7
<211> LENGTH: 1910
<212> TYPE: DNA
<213> ORGANISM: Unknown
<220> FEATURE:
<223> OTHER INFORMATION: artificial cry2Ae DNA sequence for expression
      in cotton
<220> FEATURE:
<221> NAME/KEY: CDS
<222> LOCATION: (3)..(1901)
<223> OTHER INFORMATION:

<400> SEQUENCE: 7 cc atg gct aac aac gtt ctt aac aac ggt agg act act att tgc gat         47
   Met Ala Asn Asn Val Leu Asn Asn Gly Arg Thr Thr Ile Cys Asp
   1               5                   10                  15 gca tac aac gtt gtt gct cat gat cct ttc tct ttc gag cat aag tct       95
Ala Tyr Asn Val Val Ala His Asp Pro Phe Ser Phe Glu His Lys Ser
                20                  25                  30 ctt gat aca att agg aag gag tgg atg gag tgg aag agg act gat cat     143
Leu Asp Thr Ile Arg Lys Glu Trp Met Glu Trp Lys Arg Thr Asp His
        35                  40                  45 tct ctt tac gtt gct cct att gtt ggt act gtt tct tct ttc ctt ctt     191
Ser Leu Tyr Val Ala Pro Ile Val Gly Thr Val Ser Ser Phe Leu Leu
50                  55                  60
```

```
aag aag gtt ggt tct ctt atc ggt aag agg atc ctt tct gag ctt tgg      239
Lys Lys Val Gly Ser Leu Ile Gly Lys Arg Ile Leu Ser Glu Leu Trp
 65              70                  75 ggt ctt atc ttc cct tct ggt tct act aac ctt atg caa gat att ctt      287
Gly Leu Ile Phe Pro Ser Gly Ser Thr Asn Leu Met Gln Asp Ile Leu
 80              85                  90                  95 agg gag act gaa caa ttc ctt aac cag agg ctt aac act gat act ctt      335
Arg Glu Thr Glu Gln Phe Leu Asn Gln Arg Leu Asn Thr Asp Thr Leu
                100                 105                 110 gct agg gtt aac gct gag ctt gag ggt ctt caa gct aac att agg gaa      383
Ala Arg Val Asn Ala Glu Leu Glu Gly Leu Gln Ala Asn Ile Arg Glu
            115                 120                 125 ttc aac cag caa gtt gat aac ttc ctt aac cct act caa aac cct gtt      431
Phe Asn Gln Gln Val Asp Asn Phe Leu Asn Pro Thr Gln Asn Pro Val
        130                 135                 140 cct ctt tct att act tct tct gtt aac act atg caa caa ctt ttc ctt      479
Pro Leu Ser Ile Thr Ser Ser Val Asn Thr Met Gln Gln Leu Phe Leu
145                 150                 155 aac agg ctt cct caa ttc agg gtt caa ggt tac caa ctt ctt ctt ctt      527
Asn Arg Leu Pro Gln Phe Arg Val Gln Gly Tyr Gln Leu Leu Leu Leu
160                 165                 170                 175 cct ctt ttc gct caa gct gct aac atg cac cta agc ttc att agg gat      575
Pro Leu Phe Ala Gln Ala Ala Asn Met His Leu Ser Phe Ile Arg Asp
                180                 185                 190 gtt gtt ctt aac gct gat gag tgg ggt att tct gct gct act ctt agg      623
Val Val Leu Asn Ala Asp Glu Trp Gly Ile Ser Ala Ala Thr Leu Arg
            195                 200                 205 act tac caa aac tac ctt aag aac tac act act gag tac tct aac tac      671
Thr Tyr Gln Asn Tyr Leu Lys Asn Tyr Thr Thr Glu Tyr Ser Asn Tyr
        210                 215                 220 tgc att aac act tac caa act gct ttc agg ggt ctt aac act agg ctt      719
Cys Ile Asn Thr Tyr Gln Thr Ala Phe Arg Gly Leu Asn Thr Arg Leu
225                 230                 235 cat gat atg ctt gag ttc agg act tac atg ttc ctt aac gtt ttc gag      767
His Asp Met Leu Glu Phe Arg Thr Tyr Met Phe Leu Asn Val Phe Glu
240                 245                 250                 255 tac gtt tct att tgg tct ctt ttc aag tac cag tct ctt ctt gtt tct      815
Tyr Val Ser Ile Trp Ser Leu Phe Lys Tyr Gln Ser Leu Leu Val Ser
                260                 265                 270 tct ggt gct aac ctt tac gct tct ggt tct ggt cct caa caa act caa      863
Ser Gly Ala Asn Leu Tyr Ala Ser Gly Ser Gly Pro Gln Gln Thr Gln
            275                 280                 285 tct ttc act tct caa gac tgg cct ttc ctt tac tct ctt ttc caa gtt      911
Ser Phe Thr Ser Gln Asp Trp Pro Phe Leu Tyr Ser Leu Phe Gln Val
        290                 295                 300 aac tct aac tac gtt ctt aac ggt ttc tct ggt gct agg ctt act caa      959
Asn Ser Asn Tyr Val Leu Asn Gly Phe Ser Gly Ala Arg Leu Thr Gln
305                 310                 315 act ttc cct aac atc ggt ggt ctt cct ggt act act act cat gct      1007
Thr Phe Pro Asn Ile Gly Gly Leu Pro Gly Thr Thr Thr His Ala
320                 325                 330                 335 ctt ctt gct gct agg gtt aac tac tct ggt ggt gtt tct tct ggt gat      1055
Leu Leu Ala Ala Arg Val Asn Tyr Ser Gly Gly Val Ser Ser Gly Asp
                340                 345                 350 atc ggt gct gtt ttc aac cag aac ttc tct tgc tct act ttc ctt cct      1103
Ile Gly Ala Val Phe Asn Gln Asn Phe Ser Cys Ser Thr Phe Leu Pro
            355                 360                 365 cct ctt ctt act cct ttc gtt agg tct tgg ctt gat tct ggt tct gat      1151
Pro Leu Leu Thr Pro Phe Val Arg Ser Trp Leu Asp Ser Gly Ser Asp
        370                 375                 380
```

```
agg ggt ggt gtt aac act gtt act aac tgg caa act gag tct ttc gag    1199
Arg Gly Gly Val Asn Thr Val Thr Asn Trp Gln Thr Glu Ser Phe Glu
    385                 390                 395 tct act ctt ggt ctt agg tgc ggt gct ttc act gct agg ggt aac tct    1247
Ser Thr Leu Gly Leu Arg Cys Gly Ala Phe Thr Ala Arg Gly Asn Ser
400                 405                 410                 415 aac tac ttc cct gat tac ttc att agg aac att tct ggt gtt cct ctt    1295
Asn Tyr Phe Pro Asp Tyr Phe Ile Arg Asn Ile Ser Gly Val Pro Leu
                420                 425                 430 gtt gtt agg aac gag gat ctt agg agg cct ctt cat tac aac gag att    1343
Val Val Arg Asn Glu Asp Leu Arg Arg Pro Leu His Tyr Asn Glu Ile
            435                 440                 445 agg aac att gag tct cct tct ggt act cct ggt ggt ctt agg gct tac    1391
Arg Asn Ile Glu Ser Pro Ser Gly Thr Pro Gly Gly Leu Arg Ala Tyr
        450                 455                 460 atg gtt tct gtt cat aac agg aag aac aac atc tac gct gtt cat gag    1439
Met Val Ser Val His Asn Arg Lys Asn Asn Ile Tyr Ala Val His Glu
    465                 470                 475 aac ggt act atg att cat ctt gct cct gag gat tac acc ggt ttc acc    1487
Asn Gly Thr Met Ile His Leu Ala Pro Glu Asp Tyr Thr Gly Phe Thr
480                 485                 490                 495 atc tcc ccc atc cac gcc acc cag gtc aat aat cag acc agg acc ttc    1535
Ile Ser Pro Ile His Ala Thr Gln Val Asn Asn Gln Thr Arg Thr Phe
                500                 505                 510 atc tcc gag aag ttc ggc aac cag ggc gac tcc ctg agg ttc gag cag    1583
Ile Ser Glu Lys Phe Gly Asn Gln Gly Asp Ser Leu Arg Phe Glu Gln
            515                 520                 525 tcc aac acc acc gcc agg tac acc ctg agg ggc aac ggc aac tcc tac    1631
Ser Asn Thr Thr Ala Arg Tyr Thr Leu Arg Gly Asn Gly Asn Ser Tyr
        530                 535                 540 aac ctg tac ctc agg gtg tcc tcc ctc ggc aac tcc acc atc agg gtc    1679
Asn Leu Tyr Leu Arg Val Ser Ser Leu Gly Asn Ser Thr Ile Arg Val
    545                 550                 555 acc atc aac ggc agg gtg tac acc gcc tcc aac gtg aac acc acc acc    1727
Thr Ile Asn Gly Arg Val Tyr Thr Ala Ser Asn Val Asn Thr Thr Thr
560                 565                 570                 575 aac aac gac ggc gtc aac gac aac ggc gct agg ttc ctg gac atc aac    1775
Asn Asn Asp Gly Val Asn Asp Asn Gly Ala Arg Phe Leu Asp Ile Asn
                580                 585                 590 atg ggc aac gtc gtg gcc tcc gac aac acc aac gtg ccc ctg gac atc    1823
Met Gly Asn Val Val Ala Ser Asp Asn Thr Asn Val Pro Leu Asp Ile
            595                 600                 605 aac gtg aca ttt aac tcc ggc acc cag ttc gag ctg atg aac atc atg    1871
Asn Val Thr Phe Asn Ser Gly Thr Gln Phe Glu Leu Met Asn Ile Met
        610                 615                 620 ttc gtg cca act aac ctc cca ccc atc tac tgagctagc                   1910
Phe Val Pro Thr Asn Leu Pro Pro Ile Tyr
    625                 630

<210> SEQ ID NO 8
<211> LENGTH: 633
<212> TYPE: PRT
<213> ORGANISM: Unknown
<220> FEATURE:
<223> OTHER INFORMATION: Artificial Sequence

<400> SEQUENCE: 8

Met Ala Asn Asn Val Leu Asn Asn Gly Arg Thr Thr Ile Cys Asp Ala
1               5                   10                  15

Tyr Asn Val Val Ala His Asp Pro Phe Ser Phe Glu His Lys Ser Leu
                20                  25                  30
```

Asp Thr Ile Arg Lys Glu Trp Met Glu Trp Lys Arg Thr Asp His Ser
         35                  40                  45

Leu Tyr Val Ala Pro Ile Val Gly Thr Val Ser Ser Phe Leu Leu Lys
     50                  55                  60

Lys Val Gly Ser Leu Ile Gly Lys Arg Ile Leu Ser Glu Leu Trp Gly
 65                  70                  75                  80

Leu Ile Phe Pro Ser Gly Ser Thr Asn Leu Met Gln Asp Ile Leu Arg
                 85                  90                  95

Glu Thr Glu Gln Phe Leu Asn Gln Arg Leu Asn Thr Asp Thr Leu Ala
            100                 105                 110

Arg Val Asn Ala Glu Leu Glu Gly Leu Gln Ala Asn Ile Arg Glu Phe
        115                 120                 125

Asn Gln Gln Val Asp Asn Phe Leu Asn Pro Thr Gln Asn Pro Val Pro
    130                 135                 140

Leu Ser Ile Thr Ser Ser Val Asn Thr Met Gln Gln Leu Phe Leu Asn
145                 150                 155                 160

Arg Leu Pro Gln Phe Arg Val Gln Gly Tyr Gln Leu Leu Leu Leu Pro
                165                 170                 175

Leu Phe Ala Gln Ala Ala Asn Met His Leu Ser Phe Ile Arg Asp Val
            180                 185                 190

Val Leu Asn Ala Asp Glu Trp Gly Ile Ser Ala Ala Thr Leu Arg Thr
        195                 200                 205

Tyr Gln Asn Tyr Leu Lys Asn Tyr Thr Thr Glu Tyr Ser Asn Tyr Cys
    210                 215                 220

Ile Asn Thr Tyr Gln Thr Ala Phe Arg Gly Leu Asn Thr Arg Leu His
225                 230                 235                 240

Asp Met Leu Glu Phe Arg Thr Tyr Met Phe Leu Asn Val Phe Glu Tyr
                245                 250                 255

Val Ser Ile Trp Ser Leu Phe Lys Tyr Gln Ser Leu Leu Val Ser Ser
            260                 265                 270

Gly Ala Asn Leu Tyr Ala Ser Gly Ser Gly Pro Gln Gln Thr Gln Ser
        275                 280                 285

Phe Thr Ser Gln Asp Trp Pro Phe Leu Tyr Ser Leu Phe Gln Val Asn
    290                 295                 300

Ser Asn Tyr Val Leu Asn Gly Phe Ser Gly Ala Arg Leu Thr Gln Thr
305                 310                 315                 320

Phe Pro Asn Ile Gly Gly Leu Pro Gly Thr Thr Thr His Ala Leu
                325                 330                 335

Leu Ala Ala Arg Val Asn Tyr Ser Gly Gly Val Ser Ser Gly Asp Ile
        340                 345                 350

Gly Ala Val Phe Asn Gln Asn Phe Ser Cys Ser Thr Phe Leu Pro Pro
    355                 360                 365

Leu Leu Thr Pro Phe Val Arg Ser Trp Leu Asp Ser Gly Ser Asp Arg
    370                 375                 380

Gly Gly Val Asn Thr Val Thr Asn Trp Gln Thr Glu Ser Phe Glu Ser
385                 390                 395                 400

Thr Leu Gly Leu Arg Cys Gly Ala Phe Thr Ala Arg Gly Asn Ser Asn
                405                 410                 415

Tyr Phe Pro Asp Tyr Phe Ile Arg Asn Ile Ser Gly Val Pro Leu Val
            420                 425                 430

Val Arg Asn Glu Asp Leu Arg Arg Pro Leu His Tyr Asn Glu Ile Arg
        435                 440                 445

Asn Ile Glu Ser Pro Ser Gly Thr Pro Gly Gly Leu Arg Ala Tyr Met

```
                  450                 455                 460
Val Ser Val His Asn Arg Lys Asn Asn Ile Tyr Ala Val His Glu Asn
465                 470                 475                 480

Gly Thr Met Ile His Leu Ala Pro Glu Asp Tyr Thr Gly Phe Thr Ile
                    485                 490                 495

Ser Pro Ile His Ala Thr Gln Val Asn Asn Gln Thr Arg Thr Phe Ile
                500                 505                 510

Ser Glu Lys Phe Gly Asn Gln Gly Asp Ser Leu Arg Phe Glu Gln Ser
            515                 520                 525

Asn Thr Thr Ala Arg Tyr Thr Leu Arg Gly Asn Gly Asn Ser Tyr Asn
        530                 535                 540

Leu Tyr Leu Arg Val Ser Ser Leu Gly Asn Ser Thr Ile Arg Val Thr
545                 550                 555                 560

Ile Asn Gly Arg Val Tyr Thr Ala Ser Asn Val Asn Thr Thr Thr Asn
                    565                 570                 575

Asn Asp Gly Val Asn Asp Asn Gly Ala Arg Phe Leu Asp Ile Asn Met
                580                 585                 590

Gly Asn Val Val Ala Ser Asp Asn Thr Asn Val Pro Leu Asp Ile Asn
            595                 600                 605

Val Thr Phe Asn Ser Gly Thr Gln Phe Glu Leu Met Asn Ile Met Phe
610                 615                 620

Val Pro Thr Asn Leu Pro Pro Ile Tyr
625                 630

<210> SEQ ID NO 9
<211> LENGTH: 1910
<212> TYPE: DNA
<213> ORGANISM: Unknown
<220> FEATURE:
<223> OTHER INFORMATION: artificial cry2Ae DNA sequence for expression
      in corn

<400> SEQUENCE: 9
ccatggctaa caacgtgctg aacaacggca ggaccaccat ctgcgatgca tacaacgtgg      60
tggcccacga cccattcagc ttcgagcaca gagcctggga caccatccgc aaggagtgga     120
tggagtggaa gcgcaccgac acagcctgt acgtggcccc tatcgtgggc accgtgagca     180
gcttcctgct gaagaaggtg ggcagcctga tcggcaagag gatcctgagc gagctgtggg     240
gcctgatctt cccaagcggc agcaccaacc tgatgcagga catcctgagg gagaccgagc     300
agttcctgaa ccagcgcctg aacaccgaca ccctggctcg cgtgaacgcc gagctggagg     360
gcctccaggc caacatcagg gaattcaacc agcaggtgga caacttcctg aacccaaccc     420
agaacccagt gccactgagc atcaccagca gcgtgaacac catgcagcag ctgttcctga     480
accgcctgcc acagttccgc gtgcagggct accagctgct gctgctgcca ctgttcgccc     540
aggctgccaa catgcaccta agcttcatcc gcgacgtggt gctgaacgcc gacgagtggg     600
gcatcagcgc tgccaccctg cgcacctacc agaactacct gaagaactac accaccgagt     660
acagcaacta ctgcatcaac acctaccaga ccgccttcag gggcctgaac accaggctgc     720
acgacatgct ggagttccgc acctacatgt tcctgaacgt gttcgagtac gtgagcatct     780
ggagcctgtt caagtaccag agcctgctgg tgagcagcgg tgccaacctg tacgccagcg     840
gcagcggtcc acagcagacc cagagcttca ccagccagga ctggcccttc ctgtacagcc     900
tgttccaggt gaacagcaac tacgtgctga acggcttcag cggtgccagg ctgacccaga     960
ccttcccaaa catcggaggc ctgccaggca ccaccaccac ccacgccctg ctggctgcca    1020
```

```
gggtgaacta cagcggtggc gtgagcagcg gcgatatcgg cgctgtgttc aaccagaact    1080
tcagctgcag caccttcctg ccaccactgc tgacccatt cgtgcgcagc tggctggaca     1140
gcggcagcga caggggtggc gtgaacaccg tgaccaactg gcagaccgag agcttcgaga    1200
gcaccctggg cctgcgctgc ggtgccttca ccgccagggg caacagcaac tacttcccag    1260
actacttcat ccgcaacatc agcggcgtgc cactggtggt gcgcaacgag gacctgcgca    1320
ggccactgca ctacaacgag atccgcaaca tcgagagccc aagcggcacc ccaggaggcc    1380
tgagggccta catggtgagc gtgcacaacc gcaagaacaa catctacgcc gtgcacgaga    1440
acggcaccat gatccacctg gccccagagg actacaccgg tttcaccatc tcccccatcc    1500
acgccaccca ggtcaataat cagaccagga ccttcatctc cgagaagttc ggcaaccagg    1560
gcgactccct gaggttcgag cagtccaaca ccaccgccag gtacaccctg aggggcaacg    1620
gcaactccta caacctgtac ctcagggtgt cctccctcgg caactccacc atcagggtca    1680
ccatcaacgg cagggtgtac accgcctcca acgtgaacac caccaccaac aacgacggcg    1740
tcaacgacaa cggcgctagg ttcctggaca tcaacatggg caacgtcgtg gcctccgaca    1800
acaccaacgt gccctggac atcaacgtga catttaactc cggcacccag ttcgagctga     1860
tgaacatcat gttcgtgcca actaacctcc cacccatcta ctgagctagc               1910
```

BACILLUS THURINGIENSIS INSECTICIDAL PROTEINS

This application is a divisional of U.S. patent application Ser. No. 11/783,379, filed Apr. 9, 2007, now abandoned, which is a divisional of U.S. patent application Ser. No. 10/040,906, filed Jan. 9, 2002, now U.S. Pat. No. 7,244,880, which claims benefit of U.S. Provisional Patent Application No. 60/331,355, filed Jan. 9, 2001, the disclosures of each of which are hereby incorporated by reference.

BACKGROUND OF THE INVENTION (i) Field of the Invention

The present invention relates to new nucleic acid sequences, particularly DNA sequences, encoding insecticidal proteins produced by *Bacillus thuringiensis* strains. Particularly, new nucleic acid sequences, particularly DNA sequences encoding proteins designated as Cry2Ae, Cry2Af and Cry2Ag are provided which are useful to protect plants from insect damage. Also included herein are micro-organisms and plants transformed with a nucleic acid sequence, particularly a DNA sequence, encoding at least one of the newly isolated Cry2A proteins.

(ii) Description of Related Art

*Bacillus thuringiensis* (abbreviated herein as "Bt") is well known for its specific toxicity to insect pests, and has been used since almost a century to control insect pests of plants. In more recent years, transgenic plants expressing Bt proteins were made which were found to successfully control insect damage on plants (e.g., Vaeck at al., 1987, Jansens et al., 1997).

Despite the isolation of quite a number of insecticidal Bt genes, the search for new genes encoding insecticidal proteins continues. Indeed, insecticidal Bt proteins are known to have a relatively narrow target insect range compared to chemical insecticides. Also, having multiple toxins to the same target insect species allows the use of proteins having different modes of action so that insect resistance development can be prevented or delayed. And, insecticidal Bt proteins with different amino acid sequences have different levels of insecticidal efficacy against specific insects, making it desirable to have several different insecticidal proteins available in order to be able to control the relevant insect pests of different crop plants.

Previously, several types of Cry2A-proteins were identified (see Crickmore et al., 1998, incorporated herein by reference).

The new Cry2Ae protein of this invention has the highest amino acid sequence identity to the Cry2Aa1 protein (Donovan et al., GenBank accession number M31738), but still differs in about 9 percent of its amino acid sequence.

The closest sequence identity to the Cry2Af protein was found in the Cry2Ab1 protein (Widner and Whiteley, GenBank accession number M23724), but both proteins still differ in about 5 percent of their amino acid sequence.

The closest sequence identity to the Cry2Ag protein was found in the Cry2Ac1 protein (Wu et al., GenBank accession number X57252), but both proteins still differ in about 20 percent of their amino acid sequence.

Further known Cry2A proteins include the Cry2Ad1 protein (Choi et al., 1999), and other Cry2Aa, Cry2Ab, and Cry2Ac proteins (Crickmore et al., 1998). Cry2A-like proteins and DNA sequences encoding them are also shown in U.S. Pat. No. 5,338,544, in published PCT patent application WO 00/26371 and in published PCT patent application WO 98/40490.

Expression of Cry2A-type proteins in plants has been described, e.g., in Kota et al. (1999) and in published PCT patent application WO 00/26371.

SUMMARY AND OBJECTS OF THE INVENTION

In accordance with this invention, there is provided a nucleic acid sequence, particularly a DNA sequence, encoding a protein comprising the amino acid sequence selected from the group consisting of: a) the amino acid sequence of the smallest toxic fragment of the protein encoded by the cry2Ae gene deposited at the BCCM-LMBP under accession number LMBP 4248, b) the amino acid sequence of the smallest toxic fragment of the protein encoded by the cry2Af gene deposited at the BCCM-LMBP under accession number LMBP 4247, and c) the amino acid sequence of the smallest toxic fragment of the protein encoded by the cry2Ag gene deposited at the BCCM-LMBP under accession number LMBP 4249.

Particularly preferred in accordance with this invention is a nucleic acid sequence, particularly a DNA sequence, encoding a protein comprising the amino acid sequence selected from the group consisting of: the amino acid sequence of an insecticidal fragment of the protein of SEQ ID No. 2, the amino acid sequence of an insecticidal fragment of the protein of SEQ ID No. 4, the amino acid sequence of an insecticidal fragment of the protein of SEQ ID No. 4.

Further, in accordance with this invention are provided nucleic acid sequences, particularly DNA sequences, encoding a protein comprising the amino acid sequence selected from the group consisting of: the amino acid sequence of SEQ ID No. 2 from amino acid position 1 to amino acid position 632, the amino acid sequence of SEQ ID No. 4 from amino acid position 1 to amino acid position 632, and the amino acid sequence of SEQ ID No. 6 from amino acid position 1 to amino acid position 627.

Further, in accordance with this invention are provided the above nucleic acid sequences, particularly DNA sequences, comprising an artificial sequence, having a different codon usage compared to the naturally occurring sequence, but encoding the same protein or its insecticidal fragment, preferably such codon usage resembles that of plants, particularly the host plant in which the nucleic acid sequence, particularly the DNA, is to be transformed.

Even further provided in accordance with this invention is a protein comprising the amino acid sequence selected from the group consisting of: a) the amino acid sequence of the smallest toxic fragment of the protein encoded by the cry2Ae gene deposited at the BCCM-LMBP under accession number LMBP 4248, b) the amino acid sequence of the smallest toxic fragment of the protein encoded by the cry2Af gene deposited at the BCCM-LMBP under accession number LMBP 4247, and c) the amino acid sequence of the insecticidal smallest toxic fragment of the protein encoded by the cry2Ag gene deposited at the BCCM-LMBP under accession number LMBP 4249.

Particularly preferred herein is, a protein comprising the amino acid sequence selected from the group consisting of: the amino acid sequence of an insecticidal fragment of the protein of SEQ ID No. 2, the amino acid sequence of an insecticidal fragment of the protein of SEQ ID No. 4, and the amino acid sequence of an insecticidal fragment of the protein of SEQ ID No. 6.

Also provided herein are chimeric genes comprising the DNA as defined above under the control of a plant-expressible promoter, and plant cells, plants or seeds transformed to contain those chimeric genes, particularly plant cells, plants, or seeds selected from the group consisting of: corn, cotton, rice, tobacco, oilseed rape, *Brassica* species, eggplant, soybean, potato, sunflower, tomato, sugarcane, tea, beans, tobacco, strawberry, clover, cucumber, watermelon, pepper, oat, barley, wheat, dahlia, gladiolus, chrysanthemum, sugarbeet, sorghum, alfalfa, apple, pear, strawberry, and peanut. In accordance with this invention, the chimeric gene can be integrated in the nuclear, plastid or mitochondrial DNA of the plant cells, or can also contain a DNA encoding an effective targeting or transit peptide for targeting to the vacuole, chloroplast, mitochondrium, plastid, or for secretion.

Further in accordance with this invention are provided micro-organisms, transformed to contain any of the above DNA sequences, particularly those selected from the genus *Pseudomonas, Agrobacterium, Escherichia*, or *Bacillus*.

Also provided herein is a process for controlling insects, comprising expressing any of the above nucleic acid sequences, particularly DNA sequences, in a host cell, particularly plant cells, and contacting insects with said host cells, and a process for rendering a plant resistant to insects, comprising transforming plants cells with any of the above DNA sequences or chimeric genes, and regenerating transformed plants from such cells which are resistant to insects.

This invention also relates to a method for controlling lepidopteran insects, particularly lepidopteran insect pests of cotton, corn or soybean, which method comprises applying to an area or plant to be protected, a Cry2A protein as defined herein, preferably a Cry2Ae protein as defined herein, (i.e., by planting a plant transformed with a cry2A gene of this invention, or by spraying a composition containing a Cry2A protein of this invention). The invention also relates to the use of the Cry2A proteins of this invention, particularly the Cry2Ae protein, against Lepidopteran insect pests to minimize damage to soybean plants.

This invention further relates to a method for controlling lepidopteran rice insect pests, particularly Lepidopteran rice stemborers, rice skippers, rice cutworms, rice armyworms, rice caseworms or rice leaffolders, preferably an insect selected from the group consisting of: *Chilo suppressalis, Chilo partellus, Scirpophaga incertulas, Sesamia inferens, Cnaphalocrocis medinalis, Marasmia patnalis, Marasmia exigua, Marasmia ruralis, Scirpophaga innotata*, which method comprises applying to an area or plant to be protected, a Cry2A protein as defined herein, preferably a Cry2Ae protein as defined herein, (i.e., by planting a rice plant transformed with a cry2A gene of this invention, or spraying a composition containing a Cry2A protein of this invention). The invention also relates to the use of the Cry2A proteins of this invention, particularly the Cry2Ae protein, against Lepidopteran rice insect pests to minimize damage to rice plants.

DETAILED DESCRIPTION OF PREFERRED
EMBODIMENTS OF THE INVENTION

In accordance with this invention, a "nucleic acid sequence" refers to a DNA or RNA molecule in single or double stranded form, preferably a DNA or RNA, particularly a DNA, encoding any of the Cry2A proteins of this invention. An "isolated nucleic acid sequence", as used herein, refers to a nucleic acid sequence which is no longer in the natural environment where it was isolated from, e.g., the nucleic acid sequence in another bacterial host or in a plant nuclear genome.

In accordance with this invention, the terms "protein" or "polypeptide" are used interchangeably to refer to a sequence of amino acids, without reference to any functionality, size, three-dimensional structures or origin. Hence, a fragment or portion of a Cry2A protein of the invention is still referred to herein as a "protein".

In accordance with this invention, nucleic acid sequences, particularly DNA sequences, encoding new Bt Cry toxins have been isolated and characterized. The new genes were designated cry2Ae, cry2Af, cry2Ag and their encoded to proteins Cry2Ae, Cry2Af and Cry2Ag.

In accordance with this invention "Cry2Ae protein" refers to any protein comprising the smallest fragment of the amino acid sequence of SEQ ID No. 2 which retains insecticidal activity (hereinafter referred to as "smallest toxic fragment"), particularly any protein comprising the amino acid sequence from the amino acid at position 1 to the amino acid at position 625, particularly to the amino acid at position 632 in SEQ ID No. 2. This includes hybrids or chimeric proteins comprising the smallest toxic protein fragment, as well as proteins containing at least one of the three domains of the protein of SEQ ID No. 2. Also included in this definition are variants of the amino acid sequence in SEQ ID No. 2, such as proteins having a sequence identity of at least 92%, particularly at least 93%, 95%, 96%, 97%, 98% or 99% at the amino acid sequence level, as determined using pairwise alignments using the GAP program of the Wisconsin package of GCG (Madison, Wis., USA, version 10.0; use GCG defaults within the GAP program; for the amino acid sequence comparisons, use the blosum62 scoring matrix), preferably proteins having some, preferably 5-10, particularly less than 5, amino acids added, replaced or deleted without significantly changing, preferably without changing, the insecticidal activity of the protein, e.g., the Cry2Ae protein of SEQ ID No. 8.

The term "DNA/protein comprising the sequence X", as used herein, refers to a DNA or protein including or containing at least the sequence X, so that other nucleotide or amino acid sequences can be included at the 5' (or N-terminal) and/or 3' (or C-terminal) end, e.g. (the nucleotide sequence of) a selectable marker protein as disclosed in EP 0 193 259, (the nucleotide sequence of) a transit peptide, and/or a 5' or 3' leader sequence.

The "smallest toxic fragment" of a Cry protein of the invention, as used herein, is that smallest fragment or portion of a Cry protein retaining insecticidal activity that can be obtained by enzymatic, preferably trypsin or chymotrypsin, digestion of the full length Cry protein, or that smallest fragment or portion of a Cry protein retaining insecticidal activity that can be obtained by making nucleotide deletions in the DNA encoding a Cry protein. The N- and C-terminal amino acid sequence ends of the smallest toxic fragment are conveniently determined by amino acid sequence determination of the above fragments by techniques routinely available in the art. For the Cry2A protein fragments retaining insecticidal activity of this invention, typically N-terminal deletions can be made while little can be deleted at their C-terminal end. For the Cry2Ae and Cry2Af proteins of the invention, it is expected that deletions up to amino acid position 625 at the C-terminus (i.e., the C-terminal amino acid would be the amino acid at position 625) can be done while conserving the insecticidal activity, for the Cry2Ag protein, it is expected that deletions up to amino acid position 620 at the C-terminus (i.e., the C-terminal amino acid would be the amino acid at position 620) can be done while conserving the insecticidal activity of the protein. It is expected that N-terminal deletions up to around amino acid position 50, preferably N-terminal deletions up to amino acid position 50 the N-terminal amino acid would be position 50 of the sequences shown in the sequence listing) in the amino acid sequence of the three Cry2A proteins of this invention, retain most of their insecticidal activity against Lepidopteran insects.

In accordance with this invention, "Cry2Af protein" refers to any protein comprising the smallest toxic fragment of the amino acid sequence of SEQ ID No. 4, particularly any protein comprising the amino acid sequence from the amino acid at position 1 to the amino acid at position 625, particularly to the amino acid at position 632, in SEQ ID No. 4. This includes hybrids or chimeric proteins comprising the smallest toxic protein fragment, as well as proteins containing at least one of the three domains of the protein of SEQ ID No. 4. Also included in this definition are variants of the amino acid sequence in SEQ ID No. 4, such as proteins having a sequence identity of at least 95%, particularly at least 97%, at least 98% or at least 99% at the amino acid sequence level, as determined using pairwise alignments using the GAP program of the Wisconsin package of GCG (Madison, Wis., USA, version 10.0; use GCG defaults within the GAP program; for the amino acid sequence comparisons, use the blosum62 scoring to matrix), preferably proteins having some, preferably 5-10, particularly less than 5, amino acids added, replaced or deleted without significantly changing, preferably without changing, the insecticidal activity of the protein.

In accordance with this invention, "Cry2Ag protein" refers to any protein comprising the smallest toxic fragment of the amino acid sequence of SEQ ID No. 6, particularly any protein comprising the amino acid sequence from the amino acid at position 1 to the amino acid at position 620, particularly to the amino acid at position 627, in SEQ ID No. 6. This includes hybrids or chimeric proteins comprising the smallest toxic protein fragment, as well as proteins containing at least one of the three domains of the toxic fragment of SEQ ID No. 6. Also included in this definition are variants of the amino acid sequence in SEQ ID No. 6, such as proteins having a sequence identity of at least 80%, particularly at least 85%, 90%, 95%, 96%, 97%, 98%, or at least 99% at the amino acid sequence level, as determined using pairwise alignments using the GAP program of the Wisconsin package of GCG (Madison, Wis., USA, version 10.0; use GCG defaults within the GAP program; for the amino acid sequence comparisons, use the blosum62 scoring matrix), preferably proteins having some, preferably 5-10, particularly less than 5, amino acids added, replaced or deleted without significantly changing, preferably without changing, the insecticidal activity of the protein.

As used herein, the terms "cry2Ae DNA", "cry2Af DNA", or "cry2Ag DNA" refer to any DNA sequence encoding the Cry2Ae, Cry2Af or Cry2Ag protein, respectively, as defined above. This includes naturally occurring, artificial or synthetic DNA sequences encoding the proteins of SEQ ID Nos. 2, 4 or 6 or their insecticidal fragments or variants as defined above. Also included herein are DNA sequences encoding insecticidal proteins which are similar enough to the coding regions of the genomic DNA sequences deposited or the sequences provided in the sequence listing so that they can (i.e., have the ability to) hybridize to these DNA sequences under stringent hybridization conditions. Stringent hybridization to conditions, as used herein, refers particularly to the following conditions: immobilizing the relevant genomic DNA sequences on a filter, and prehybridizing the filters for either 1 to 2 hours in 50% formamide, 5% SSPE, 2×Denhardt's reagent and 0.1% SDS at 42° C. or 1 to 2 hours in 6×SSC, 2×Denhardt's reagent and 0.1% SDS at 68° C. The denatured (dig- or radio-)labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen. Of course, equivalent conditions and parameters can be used in this process while still retaining the desired stringent hybridization conditions. Preferred variants of the cry2Ae DNA of this invention are a DNA encoding the insecticidal Cry2Ae protein variants described above, or a DNA sequence encoding an insecticidal protein with at least 92%, preferably at least 93 to 97%, particularly at least 98% or at least 99%, sequence identity to the coding sequence of SEQ ID No. 1. Particularly, such DNA sequences also hybridize under stringent hybridization conditions to the cry2Ae coding sequence deposited at the BCCM-LMBP under accession number LMBP 4248, or to the coding sequence of SEQ ID No. 1.

Preferred variants of the cry2Af DNA of this invention are a DNA encoding the insecticidal Cry2Af protein variants described above, or a DNA sequence encoding an insecticidal protein with at least 95%, preferably at least 96% or 97%, more preferably at least 98% or at least 99%, sequence identity to the coding sequence of SEQ ID No. 3. Particularly, such DNA sequences also hybridize under stringent hybridization conditions to the cry2Af coding sequence deposited at the BCCM-LMBP under accession number LMBP 4247 or to the coding sequence of SEQ ID No. 3. Preferred variants of the cry2Ag DNA of this invention are a DNA encoding the Cry2Ag protein variants described above, or a DNA sequence with at least 86%, preferably 87 particularly at least 98% or at least 99%, sequence identity to the coding sequence of SEQ ID No. 5. Particularly, such DNA sequences also hybridize under stringent hybridization conditions to the to cry2Ag coding sequence deposited at the BCCM-LMBP under accession number LMBP 4249, or to the coding sequence of SEQ ID No. 5. The sequence identities referred to above are calculated using the GAP program of the Wisconsin package of GCG (Madison, Wis., USA) version 10.0 (GCG defaults are used, for these DNA sequence comparisons, the "nwsgapdna" scoring matrix is used), the stringent hybridization conditions are as defined above.

"Insecticidal activity" of a protein, as used herein, means the capacity of a protein to kill insects when such protein is fed to insects, preferably by expression in a recombinant host such as a plant. "Insect-controlling amounts" of a protein, as used herein, refers to an amount of protein which is sufficient to limit damage on a plant by insects feeding on such plant to commercially acceptable levels, e.g. by killing the insects or by inhibiting the insect development, fertility or growth in such a manner that they provide less damage to a plant and plant yield is not significantly adversely affected.

In accordance with this invention, insects susceptible to the new Cry proteins of the invention are contacted with this protein in insect-controlling amounts, preferably insecticidal amounts. Preferred target insects for the proteins of this invention are economically damaging insect pests of corn, cotton, rice and soybean plants, particularly in Northern and Southern American countries. Particularly preferred target insects for the Cry2A proteins of this invention, particularly the Cry2Ae protein, are *Heliothis* spp., *Helicoverpa* spp., *Spodoptera* spp., *Sesamia* spp., *Anticarsia* spp., *Ostrinia* spp., *Chilo* spp., *Sesamia* spp., *Marasmia* spp., *Scirpophaga* spp. and *Cnaphalocrocis* spp. insects, preferably, most preferably *Heliothis virescens, Helicoverpa zea, Helicoverpa armigera, Anticarsia gemmatalis* and *Ostrinia nubilalis.*

The terms "Cry2A protein", "Cry2A protein of this invention", "Cry protein", or "Cry protein of this invention", as used herein, refer to any one of the new proteins isolated in accordance with this invention and identified and defined herein as Cry2Ae, Cry2Af or Cry2Ag protein. A Cry protein, as used herein, can be a protein in the full length size, also named a protoxin, or can be in a truncated form as long as the insecticidal activity is retained, or can be a combination of different proteins in a hybrid or fusion protein. A "Cry protoxin" refers to the full length crystal protein as it is encoded by the naturally-occurring Bt DNA sequence, a "Cry toxin" refers to an insecticidal fragment thereof, particularly the smallest toxic fragment thereof, typically in the molecular weight range of about 50-65 kD, particularly about 60 kD, as determined by SDS-PAGE electrophoresis. A "cry gene", "cry2A gene", "cry DNA" or "cry2A DNA", as used herein, is a DNA sequence encoding a Cry protein in accordance with this invention, referring to any of the cry2Ae, cry2Af or cry2Ag DNA sequences defined above.

The nucleic acid sequence, particularly DNA sequence, encoding the Cry proteins of this invention can be isolated in a conventional manner from the recombinant *E. coli* strains, deposited in accordance with the Budapest Treaty on Oct. 6, 2000 at the Vakgroep voor Moleculaire Biologie-Plasmidencollectie, Universiteit Gent, K. L. Ledeganckstraat 35, B-9000 Gent, Belgium (hereinafter abbreviated as "BCCM-LMBP") under the following accession numbers: BCCM-LMBP 4247 for strain XL1Blue:pUC1099E/cry2clone1, which encodes the Cry2Af protein; BCCM-LMBP 4248 for strain XL1Blue:pUC1099E/cry2clone7, which encodes the Cry2Ae protein; and BCCM-LMBP 4249 for strain XL1Blue:pUC2761A/cry2clone141, which encodes the Cry2Ag protein. The DNA sequences encoding the Cry proteins of the invention can be isolated from these deposited strains using routine techniques, and can be inserted in expression vectors to produce high amounts of Cry proteins. The Cry proteins can be used to prepare specific monoclonal or polyclonal antibodies in a conventional manner (Höfte et al., 1988).

Also, DNA sequences for use in this invention can be synthetically made. Indeed, because of the degeneracy of the genetic code, some amino acid codons can be replaced by others without changing the amino acid sequence of the protein. Furthermore, some amino acids can be substituted by other equivalent amino acids without significantly changing, preferably without changing, the insecticidal activity of the protein. Also, changes in amino acid sequence or composition in in regions of the molecule, different from those responsible for binding or pore formation are less likely to cause a difference in insecticidal activity of the protein. Equivalents of the DNA sequences of the invention include DNA sequences hybridizing to the DNA sequence of the Cry proteins of SEQ ID. No. 1, 3, or 5 under stringent hybridization conditions and encoding a protein with the same insecticidal characteristics as the protein of this invention, or DNA sequences having a different codon usage compared to the native cry2A genes of this invention but which encode a protein with the same insecticidal activity and with substantially the same, preferably the same, amino acid sequence. Examples of codon-optimized DNA sequences for the Cry2Ae protein of this invention are found in SEQ ID Nos. 7 and 9. These DNA sequences were optimized by adapting the codon usage to that most preferred in plant genes, particularly to genes native to the plant genus or species of interest (Bennetzen & Hall, 1982; Itakura et al., 1977) using available codon usage tables (SEQ ID No. 7 was more adapted towards expression in cotton, SEQ ID No. 9 more towards corn), and also to eliminate stretches of AT or GC nucleotides longer then 5 or 6, preferably longer then 5, nucleotides, and also to insert suitable restriction sites.

Also, the N-terminus of a Cry protein can be modified to have an optimum translation initiation context, thereby adding or deleting one or more amino acids at the N-terminal end of the protein. In most cases, it is preferred that the proteins of the invention to be expressed in plants cells start with a Met-Asp or Met-Ala dipeptide for optimal translation initiation, requiring the insertion in the cry2A DNA of a codon encoding an Asp or Ala amino acid downstream of the start codon as a new second codon.

Of course, any DNA sequence differing in its codon usage but encoding the same protein or a similar protein with substantially the same insecticidal activity, can be constructed, depending on the particular purpose. It has been described in prokaryotic and eucaryotic expression systems that changing the codon usage to that of the host cell is desired for gene expression in foreign hosts (Bennetzen & Hall, 1982; Itakura et al., 1977). Furthermore, Bt crystal protein genes are known to have no bias towards eucaryotic codons, and to be very AT-rich (Adang et al., 1985, Schnepf et al., 1985). Codon usage tables are available in the literature (Wada et al., 1990; Murray et al., 1989) and in the major DNA sequence databases (e.g. EMBL at Heidelberg, Germany). Accordingly, synthetic DNA sequences can be constructed so that the same or substantially the same proteins are produced. It is evident that several DNA sequences can be made once the amino acid sequence of the Cry proteins of this invention is known. Such other DNA sequences include synthetic or semi-synthetic DNA sequences that have been changed in order to inactivate certain sites in the gene, e.g. by selectively inactivating certain cryptic regulatory or processing elements present in the native sequence as described in PCT publications WO 91/16432 and WO 93/09218, or by adapting the overall codon usage to that of a more related host organism, preferably that of the host organism in which expression is desired. Several techniques for modifying the codon usage to that preferred by the host cells can be found in patent and scientific literature. The exact method of codon usage modification is not critical for this invention as long as most or all of the cryptic regulatory sequences or processing elements have been replaced by other sequences. Examples of DNA sequences optimized for expression in plants are shown in enclosed SEC) ID Nos. 7 and 9.

Small modifications to a DNA sequence such as described above can be routinely made, i.e., by PCR-mediated mutagenesis (Ho et al., 1989, White et al., 1989). More profound modifications to a DNA sequence can be routinely done by de novo DNA synthesis of a desired coding region using available techniques.

With the term "substantially the same", when referring to the amino acid sequence of a Cry protein, is meant to include an amino acid sequence that differs in no more than 5%, preferably no more than 2%, to the amino acid sequence of the protein compared to; and when referring to toxicity of Cry protein, is meant to include a protein whose $LC_{50}$ value obtained under the same conditions of bio-assay differs by no more then 10%, preferably no more than 5%, of the $LC_{50}$ value obtained for the protein compared to.

The term "domain" of a Cry toxin as used herein means any part(s) or domain(s) of the toxin with a specific structure that can be transferred to another (Cry) protein for providing a new hybrid protein with at least one functional characteristic (e.g., the binding and/or toxicity characteristics) of the Cry toxin of the invention (Ge et al., 1991). Such parts can form an essential feature of the hybrid Bt protein with the binding and/or toxicity characteristics of the Cry protein of this invention. Such a hybrid protein can have an enlarged host range, an improved toxicity and/or can be used in a strategy to prevent insect resistance development (European Patent Publication ("EP") 408 403; Visser et al., 1993).

The cry DNA sequences of the invention, prepared from total DNA, can be ligated in suitable expression vectors and transformed in *E. coli*, and the clones can then be screened by conventional colony immunoprobing methods (French et al., 1986) for expression of the toxin with monoclonal or polyclonal antibodies raised against the Cry proteins.

Also, the cry DNA of the invention, can be ligated in suitable Bt shuttle vectors (Lereclus et al., 1992) and transformed in a crystal minus Bt-mutant. The clones can then be screened for production of crystals (detected by microscopy) or crystal proteins (detected by SDS-PAGE), or can be tested for their insecticidal activity compared to the control crystal-minus strain.

The genes encoding the Cry proteins of this invention can be sequenced in a conventional manner (Maxam and Gilbert, 1980; Sanger, 1977) to obtain the DNA sequence. Sequence comparisons indicated that the genes are different from previously described genes encoding protoxins and toxins with activity against *Lepidoptera* (see, e.g., Höfte and Whiteley, 1989; Crickmore, et al., 1998; and the Oct. 16, 2000 update on the Bt nomenclature website corresponding to the Crickmore et al. (1998) publication, found at: http://epunix.biols.susx-.ac.uk/Home/Neil_Crickmore/Bt/index.html). Also, the Cry2A proteins of in the invention are novel over any of the *Bacillus thuringiensis* crystal protein sequences in the Dec. 13, 2001 update of this 81 nomenclature website.

An insecticidally effective part of the DNA sequences, encoding an insecticidally effective portion of the newly identified Cry protein protoxin forms, can be made in a conventional manner after sequence analysis of the gene. In such fragments, it is preferred that at least the sequence homologous to the conserved sequence block 5 of Bt crystal proteins (Hofte & Whiteley, 1989; Schnepf et al., 1998) is included in such protein, preferably up to two amino acids after this homologous region. For the Cry2Ae and Cry2Af proteins, this homologous region ends at amino acid position 625 in SEQ ID Nos. 2 and 4, respectively, for Cry2Ag at position 620 in SEQ ID No. 6. The amino acid sequence of the Cry proteins can be determined from the DNA sequence of the isolated DNA sequences. By "an insecticidally effective part (or portion or fragment)" of DNA sequences encoding the Cry protein, also referred to herein as "truncated gene" or "truncated DNA", is meant a DNA sequence encoding a polypeptide which has fewer amino acids than the Cry protein protoxin form but which is insecticidal.

In order to express all or an insecticidally effective part of the DNA sequence encoding a Cry protein of this invention in *E. coli*, in other Bt strains and in plants, suitable restriction sites can be introduced, flanking the DNA sequence. This can be done by site-directed mutagenesis, using well-known procedures (Stanssens et al., 1989; White et al., 1989). In order to obtain improved expression in plants, the codon usage of the cry gene or insecticidally effective cry gene part of this invention can be modified to form an equivalent, modified or artificial gene or gene part in accordance with PCT publications WO 91/16432 and WO 93/09218; EP 0 358 962 and EP 0 359 472, or the Bt genes or gene parts can be inserted in the plastid, mitochondrial or chloroplast genome and expressed there using a suitable promoter (e.g., Mc Bride et al., 1995; U.S. Pat. No. 5,693,507). For obtaining enhanced expression in monocot plants such as corn, an intron, preferably a monocot intron, also can be added to the chimeric gene, and the DNA sequence of the cry gene or its insecticidal part can be further changed in a translationally to neutral manner, to modify possibly inhibiting DNA sequences present in the gene part by means of site-directed intron insertion and/or by introducing changes to the codon usage, e.g., adapting the codon usage to that most preferred by plants, preferably the specific relevant plant genus, (Murray et al., 1989) without changing significantly, preferably without changing, the encoded amino acid sequence.

In accordance with one embodiment of this invention, it is preferred that the proteins are targeted to intracellular organelles such as plastids, preferably chloroplasts, mitochondria, or are secreted from the cell, potentially optimizing protein stability and/or expression. For this purpose, the chimeric genes of the invention comprise a coding region encoding a signal or target peptide, linked to the Cry protein coding region of the invention. Particularly preferred peptides to be included in the proteins of this invention are the transit peptides for chloroplast or other plastid targeting, especially duplicated transit peptide regions from plant genes whose gene product is targeted to the plastids, the optimized transit peptide of Capellades et al. (U.S. Pat. No. 5,635,618), the transit peptide of ferredoxin-NADP$^+$ oxidoreductase from spinach (Oelmuller et al., 1993), the transit peptide described in Wong et al. (1992) and the targeting peptides in published PCT patent application WO 00/26371. Also preferred are peptides signalling secretion of a protein linked to such peptide outside the cell, such as the secretion signal of the potato proteinase inhibitor II (Keil et al., 1986), the secretion signal of the alpha-amylase 3 gene of rice (Sutliff at al., 1991) and the secretion signal of tobacco PR1 protein (Cornelissen et al., 1986).

Particularly useful signal peptides in accordance with the invention include the chloroplast transit peptide (e.g., Van Den Broeck et al. (1985), or the optimized chloroplast transit peptide of U.S. Pat. No. 5,510,471 and U.S. Pat. No. 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, preferably those described by Klösgen et al. (1989), Klösgen and Well (1991), Neuhaus & Rogers (1998), Bih et al. (1999), Morris et al. (1999), Hesse at al. (1989), Tavladoraki et al. (1998), Terashima at al. (1999), Park et al. (1997), Shcherban et al. (1995), all of which are incorporated herein by reference, particularly the signal peptide sequences from targeted or secreted proteins of corn, cotton, rice or soybean.

Furthermore, the binding properties of the Cry proteins of the invention can be evaluated, using methods known in the art (e.g., Van Rie et al., 1990), to determine if the Cry proteins of the invention bind to sites on the insect midgut that are not recognized (or competed for) by other, known Cry or other Bt proteins. Bt toxins with different binding sites for which there is non-competitive binding in relevant susceptible insects are very valuable to replace known Bt toxins to which insects may have developed resistance, or to use in combination with Bt toxins having a different mode of action to prevent or delay the development of insect resistance against Bt toxins, particularly when expressed in a plant. Because of the characteristics of the newly isolated Bt toxins, they are extremely useful for transforming plants, e.g. monocots such as corn or rice and dicots such as cotton, soybean and *Brassica* species plants, to protect these plants from insect damage. It has been described that in *Helicoverpa zea*, the Cry2Aa protein does not share binding sites with the Cry1Ac protein (English et al., 1994). Similarly, it is expected that the binding properties of the Cry2A proteins of the current invention will be different compared to those of Cry1 or Cry9 toxins currently used in transgenic plants in the relevant insect pests. Such different binding properties can be measured by routine binding assays as described above. Especially for insect resistance management purposes for a specific insect pest, it is preferred to combine a Cry2A protein of this invention with another insect control protein, particularly a Bt crystal protein, which does not recognize at least one binding site recognized by such Cry2A protein. Preferred insect control proteins to combine with the Cry2A proteins of this invention, preferably the Cry2Ae protein, particularly for simultaneous expression in plants, preferably cotton plants, include the Cry1F protein or hybrids derived from a Cry1F protein (e.g., the hybrid Cry1A-Cry1F proteins described in U.S. Pat. Nos. 6,326,169; 6,281, 016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275), the VIP3Aa protein or a toxic fragment thereof as described in Estruch et al., 1996 and U.S. Pat. No. 6,291,156, insecticidal proteins from *Xhenorhabdus, Serratia* or *Photorhabdus* is species strains (e.g., Waterfield et al., 2001; ffrench-Constant and Bowen, 2000). In one embodiment, such co-expression is easily obtained by transforming a plant already expressing an insect control protein with a Cry2A of this invention, or by crossing plants transformed with the insect control protein and plants transformed with the Cry2A protein of this invention. For cotton plants, preferably the Cry2Ae protein is used as first insect control protein and as second insect control protein the Cry1Ac or VIP3Aa proteins or derivatives thereof are used. Methods for obtaining expression of different Bt (or similarly, for other insect control proteins) insecticidal proteins in the same plant in an effort to minimize or prevent resistance development to transgenic insect-resistant plants are described in EP patent 0 408 403.

The Cry2A proteins of this invention can also conveniently be used to control insects in case insect resistance develops against insect control proteins, such as the Cry1 Bt proteins, which are currently already commercialized in transgenic plants.

Preferably, for selection purposes but also for increasing the weed control options, the transgenic plants of the invention are also transformed with a DNA encoding a protein conferring, resistance to a broad-spectrum herbicide, e.g., herbicides based on glufosinate or glyphosate.

The insecticidally effective cry gene part or its equivalent, preferably the cry chimeric gene, encoding an insecticidally effective portion of the Cry protoxin, can be stably inserted in a conventional manner into the nuclear genome of a single plant cell, and the so-transformed plant cell can be used in a conventional manner to produce a transformed plant that is insect-resistant. In this regard, a disarmed Ti-plasmid, containing the insecticidally effective cry gene part, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO 84/02913 and published European Patent application ("EP") 0 242 246 and in Gould et al. (1991). Preferred Ti-plasmid vectors each contain the insecticidally effective cry gene part between the border sequences, or at least located to the left of the right border sequence, of the T-DNA of the Ti-plasmid. Of course, other types of vectors can be used to transform the plant cell, using procedures such as direct gene transfer (as described, for example in EP 0.233 247), pollen mediated transformation (as described, for example in EP 0 270 356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the recently described methods for transforming certain lines of corn (e.g., U.S. Pat. No. 6,140,553; Fromm et al., 1990; Gordon-Kamm et al., 1990) and rice (Shimamolo et al., 1989; Datta et al., 1990) and the method for transforming monocots generally (PCT publication WO 92/09696). For cotton transformation, especially preferred is the method described in PCT patent publication WO 00/71733. For soybean transformation, reference is made to methods known in the art, e.g., Hinchee et al. (1988) and Christou et al. (1990) or the method of WO 00/42207.

Also, besides transformation of the nuclear genome, also transformation of the plastid genome, preferably chloroplast genome, is included in the invention. Kota et al. (1999) have described a method to overexpress a Cry2Aa protein in tobacco chloroplasts.

The resulting transformed plant can be used in a conventional plant breeding scheme to produce more transformed plants with the same characteristics or to introduce the insecticidally effective cry gene part in other varieties of the same or related plant species. Seeds, which are obtained from the transformed plants, contain the insecticidally effective cry gene part as a stable genomic insert. Cells of the transformed plant can be cultured in a conventional manner to produce the insecticidally effective portion of the Cry protoxin, preferably the Cry toxin, which can be recovered for use in conventional insecticide compositions against *Lepidoptera* (U.S. Pat. No. 5,254,799).

The insecticidally effective cry gene part, preferably the truncated cry gene, is inserted in a plant cell genome so that the inserted gene is downstream (i.e., 3') of, and under the control of, a promoter which can direct the expression of the gene part in the plant cell. This is preferably accomplished by inserting the cry chimeric gene in the plant cell genome, particularly in the nuclear or plastid (e.g., chloroplast) genome. Preferred promoters include: the strong constitutive 35S promoters (the "35S promoters") of the cauliflower mosaic virus (CaMV) of isolates CM 1841 (Gardner et al., 1981), CabbB-S (Franck et al., 1980) and CabbB-JI (Hull and Howell, 1987); the 35S promoter described by Odell et al. (1985), promoters from the ubiquitin family (e.g., the maize ubiquitin promoter of Christensen et al., 1992, see also Cornejo et al., 1993), the gos2 promoter (de Pater et al., 1992), the emu promoter (Last et al., 1990), *Arabidopsis* actin promoters such as the promoter described by An et al. (1996), rice actin promoters such as the promoter described by Zhang et al. (1991); promoters of the Cassava vein mosaic virus (WO 97/48819, Verdaguer et al. (1998)), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted cry gene part is expressed only in cells of the specific tissue(s) or organ(s). For example, the insecticidally effective cry gene part could be selectively expressed in the leaves of a plant (e.g., corn, cotton) by placing the insecticidally effective gene part under the control of a light-inducible promoter such as the promoter of the ribulose-1,5-bisphosphate carboxylase small subunit gene of the plant itself or of another plant such as pea as disclosed in U.S. Pat. No. 5,254,799. Another alternative is to use a promoter whose expression is inducible, preferably by wounding such as insect feeding, e.g., the MPI promoter described by Cordera et al. (1994), or by chemical factors.

The insecticidally effective cry gene part is inserted in the plant genome so that the inserted gene part is upstream (i.e., 5') of suitable 3' end transcription regulation signals (i.e., transcript formation and polyadenylation signals). This is preferably accomplished by inserting the cry chimeric gene in the plant cell genome. Preferred polyadenylation and transcript formation signals include those of the nopaline synthase gene (Depicker et al., 1982), the octopine synthase gene (Gielen et al., 1984) and the T-DNA gene 7 (Velten and Schell, 1985), which act as 3'-untranslated DNA sequences in transformed plant cells.

The insecticidally effective cry gene part can optionally be inserted in the plant genome as a hybrid gene (U.S. Pat. No. 5,254,799; Vaeck et al., 1987) under the control of the same promoter as a selectable or storable marker gene, such as the neo gene (EP 0 242 236) encoding kanamycin resistance, so that the plant expresses a fusion protein which is easily detectable.

Transformation of plant cells can also be used to produce the proteins of the invention in large amounts in plant cell cultures, e.g., to produce a Cry2A protein that can then be applied onto crops after proper formulation. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is not meant to refer only to isolated cells in culture, but refers to any plant cell, wherever it may be located or in whatever type of plant tissue or organ it may be present.

All or part of the cry gene, encoding an anti-lepidopteran protein, can also be used to transform other bacteria, such as a *B. thuringiensis* which has insecticidal activity against *Lepidoptera* or Coleoptera. Thereby, a transformed Bt strain can be produced which is useful for combating a wide spectrum of lepidopteran and coleopteran insect pests or for combating additional lepidopteran insect pests. Transformation of bacteria, such as bacteria of the genus *Pseudomonas*, *Agrobacterium*, *Bacillus* or *Escherichia*, with all or part of the cry gene of this invention, incorporated in a suitable cloning vehicle, can be carried out in a conventional manner, preferably using conventional electroporation techniques as described in Mahillon et al. (1989) and in PCT Patent publication WO 90/06999.

Transformed *Bacillus* species strains containing the cry gene of this invention can be fermented by conventional methods (Dulmage, 1981; Bernhard and Utz, 1993) to provide high yields of cells. Under appropriate conditions which are well understood (Dulmage, 1981), these strains each sporulate to produce crystal proteins containing the Cry protoxin in high yields.

An insecticidal, particularly anti-lepidopteran, composition of this invention can be formulated in a conventional manner using the microorganisms transformed with the cry gene, or preferably their respective Cry proteins or the Cry protoxin, toxin or insecticidally effective protoxin portion as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc.

A method for controlling insects, particularly *Lepidoptera*, in accordance with this invention can comprise applying (e.g., spraying), to a locus (area) to be protected, an insecticidal amount of the Cry proteins or host cells transformed with the cry gene of this invention. The locus to be protected can include, for example, the habitat of the insect pests or growing vegetation or an area where vegetation is to be grown.

This invention further relates to a method for controlling lepidopteran soybean insect pests, particularly Lepidopteran rice stemborers, rice skippers, rice cutworms, rice armyworms, rice caseworms or rice leaffolders, preferably an insect selected from the group consisting of: *Chilo suppressalis, Chilo partellus, Scirpophaga incertulas, Sesamia inferens, Cnaphalocrocis medinalis, Marasmia patnalis, Marasmia exigua, Marasmia ruralis, Scirpophaga innotata*, which method comprises applying to an area or plant to be protected, a Cry2A protein as defined herein, preferably a Cry2Ae protein as defined herein, (i.e., by planting a rice plant transformed with a cry2A gene of this invention, or spraying a composition containing a Cry2A protein of this invention). The invention also relates to the use of the Cry2A proteins of this invention, particularly the Cry2Ae protein, against Lepidopteran rice insect pests to minimize damage to rice plants.

This invention further relates to a method for controlling lepidopteran cotton insect pests, which method comprises applying to an area or plant to be protected, a Cry2A protein as defined herein, preferably a Cry2Ae protein as defined herein, (i.e., by planting a rice plant transformed with a cry2A gene of this invention, or spraying a composition containing a Cry2A protein of this invention). The invention also relates to the use of the Cry2A proteins of this invention, particularly the Cry2Ae protein, against Lepidopteran rice insect pests to minimize damage to rice plants.

This invention also relates to a method for controlling lepidopteran rice insect pests, particularly Lepidopteran rice stemborers, rice skippers, rice cutworms, rice armyworms, rice caseworms or rice leaffolders, preferably an insect selected from the group consisting of: *Chilo suppressalis, Chilo partellus, Scirpophaga incertulas, Sesamia inferens, Cnaphalocrocis medinalis, Marasmia patnalis, Marasmia exigua, Marasmia ruralis, Scirpophaga innotata*, which method comprises applying to an area or plant to be protected, a Cry2A protein as defined herein, preferably a Cry2Ae protein as defined herein, (i.e., by planting a rice plant transformed with a cry2A gene of this invention, or spraying a composition containing a Cry2A protein of this invention). The invention also relates to the use of the Cry2A proteins of this invention, particularly the Cry2Ae protein, against Lepidopteran rice insect pests to minimize damage to rice plants.

To obtain the Cry protoxin or toxin, cells of the recombinant hosts expressing the Cry protein can be grown in a conventional manner on a suitable culture medium and then lysed using conventional means such as enzymatic degradation or detergents or the like. The protoxin can then be separated and purified by standard techniques such as chromatography, extraction, electrophoresis, or the like. The toxin can then be obtained by trypsin digestion of the protoxin.

These and/or other embodiments of this invention are reflected in the wordings of the claims, that form part of the description of the invention.

The following Examples illustrate the invention, and are not provided to limit the invention or the protection sought. The sequence listing referred to in the Examples, the Claims and the Description is as follows Sequence Listing:
SEQ ID No. 1—amino acid and DNA sequence of Cry2Ae protein and DNA
SEQ ID No. 2—amino acid sequence of Cry2Ae protein.
SEQ ID No. 3—amino acid and DNA sequence of Cry2Af protein and DNA.
SEQ ID No. 4—amino acid sequence Cry2Af protein.
SEQ ID No. 5—amino acid and DNA sequence of Cry2Ag protein and DNA.
SEQ ID No. 6—amino acid sequence of Cry2Ag protein.
SEQ ID No. 7—artificial cry2Ae DNA sequence for expression in cotton.
SEQ ID No. 8—amino acid sequence of Cry2Ae protein encoded by the DNA of SEQ ID No. 7.
SEQ ID No. 9—artificial cry2Ae DNA sequence for expression in corn.

Unless otherwise stated in the Examples, all procedures for making and manipulating recombinant DNA are carried out by the standard procedures described in Sambrook et al., Molecular Cloning—A Laboratory Manual, Second Ed., Cold Spring Harbor Laboratory Press, NY (1989), and in Volumes 1 and 2 of Ausubel et al. (1994) Current Protocols in Molecular Biology, Current Protocols, USA. Standard materials and methods for plant molecular biology work are described in Plant Molecular Biology Labfax (1993) by R. R. D. Croy, jointly is published by BIOS Scientific Publications Ltd (UK) and Blackwell Scientific Publications (UK). Procedures for PCR technology can be found in "PCR protocols: a guide to methods and applications", Edited by M. A. Innis, D. H. Gelfand, J. J. Sninsky and T. J. White (Academic Press, Inc., 1990).

EXAMPLES

Example 1

Characterization of the Strains

The BTS02761A and BTS01099E strains were isolated from grain dust collected in the Philippines (South Tagalog) and Belgium (Deerlijk), respectively.

Each strain can be cultivated on conventional standard media, preferably $T_3$ medium (tryptone 3 tryptase 2 g/l, yeast extract 1.5 μl, 5 mg $MnCl_2$, 0.05 M $Na_2HPO_4.2H_2O$, 0.05 M $NaH_2PO_4.H_2O$, pH 6.8 and 1.5% agar), preferably at 28° C. For long term storage, it is preferred to mix an equal volume of a spore-crystal suspension with an equal volume of 50% glycerol and store this at −70° C. or lyophilize a spore-crystal suspension. For sporulation, growth on $T_3$ medium is preferred for 72 hours at 28° C., followed by storage at 4° C. The crystal proteins produced by the strains during sporulation are packaged in crystals.

Example 2

Insecticidal Activity of the BTS02761a and BTS01099E Strains Against Selected Lepidopteran Insect Species Toxicity assays were performed on neonate larvae of *Helicoverpa zea, Helicoverpa armigera. Heliothis virescens, Ostrinia nubilalis, Spodoptera frugiperda*, and *Sesamia nonagrioides* fed on an artificial diet layered with to undiluted alkaline (pH12) extract of spore-crystal mixtures from either BTS01099E or BTS02761A.

The artificial diet (Vanderzant, 1962) was dispensed in wells of Costar 48-well plates. 25 microliter of the extract on the surface of the diet and dried in a laminar air flow. One larva was placed in each well and 18 larvae were used per sample. Dead and living larvae were counted on the seventh day. The percentage of dead larvae are shown in Table I below.

Mixtures of spore/crystals from each of the strains BTS02761A and BTS01099E were tested in bioassays and gave the following results:

TABLE I

| Strain | Mortality (%) | | | | |
|---|---|---|---|---|---|
| | Hz | Hv | Sf | On | Sn |
| BTS02761A | 17* | 94 | 5 | 88 | 77 |
| BTS01099E | 70 | 100 | NT | 90 | NT |

*surviving larvae slightly affected in their growth
Negative controls (standard diet): Hz: 6% M, Hv: 17% M, Sf: 0% M.
Hz: *Helicoverpa zea*; Hv: *Heliothis virescens*; Sf: *Spodoptera frugiperda*; On: *Ostrinia nubilalis*; Sn: *Sesamia nonagroides* (NT means not tested).

Example 3

Identification and Characterization of New cry2a Genes from Bt Strains BTS01099E and BTS02761A Using appropriate primers, a portion of the cry2A gene(s) from the BTS02761A and BTS01099E strains were amplified; subsequently these amplification products were digested with restriction enzymes. The pattern obtained was then compared with the pattern that is obtained when such digests are performed on amplification products derived from strains containing known cry2A genes. Based on the to restriction digest pattern, the cry2A genes from strains BTS02761A and BTS01099E appeared to be novel. Therefore, the amplification product was sequenced. This confirmed that the amplified fragments were derived from novel cry2A genes: strain BTS02761A contained a novel cry2A-like gene, whereas strain 1099E contained two novel cry2A-like genes.

Total DNA from strains BTS02761A and BTS01099E was treated with Sau3A, size fractionated and fragments of 7 to 10 kb were ligated into pUC19I (a derivative of pUC19), cut with BamHI and treated with TsAP (heat stable alkaline phosphatase). This ligation mixture was electroporated in *E. coli* XL1 Blue.

Colony hybridizations, using the DIG-labeled PCR fragments as probes, identified positive clones. The recombinant *E. coli* strains were deposited on Oct. 6, 2000 at the Vakgroep voor Moleculaire Biologie-Plasmidencollectie, Universiteit Gent, K. L. Ledeganckstraat 35, B-9000 Gent, Belgium (hereinafter abbreviated as "BCCM-LMBP") under the following accession numbers: BCCM-LMBP 4247 for strain XL1Blue:pUC1099E/cry2clone1, which encodes a protein named Cry2Af; BCCM-LMBP 4248 for strain XL1Blue: pUC1099E/cry2clone7, which encodes a protein named Cry2Ae; and BCCM-LMBP 4249 for strain XL1Blue: pUC2761A/cry2clone141, which encodes a protein named Cry2Ag. The genes can be isolated from these deposited clones by a NotI-FseI digest.

The insert from these clones was subcloned into shuttle vector pSL40I. The resulting plasmid was first transformed into *E. coli* GM2163. A plasmid prep from this strain was then electroporated into a crystal-minus *B. thuringiensis* variety berliner 1715 strain.

An alkaline extract prepared from a spore/crystal mixture from the recombinant Bt strains was then used in bioassays to evaluate the toxicity of the novel Cry2A proteins. This extract was tested in the assay as described above in Example 1. The results are shown in Table II:

TABLE II

| Toxin | Conc. | Mortality (%) | | | | | |
|---|---|---|---|---|---|---|---|
| | | Ha | Sf | On | Sn | Hz | Hv |
| Cry2Ae | 1930 | 83 | 44 | NT | 100 | 100 | NT |
| Cry2Ag | 1160 | 0 | 0 | 78 | 50 | 29 | 100 |
| Cry2Aa | 470 | 61 | 55 | 50 | 94 | 95 | 100 |

"Conc.": total protein concentration of strain extract using the Bradford method (microgr/ml); "Ha": *Heliothis armigera*, the other abbreviations are as used above in Table I; the included controls (normal diet, PBS-BSA addition or unstransformed crystal-minus Bt strain 1715) give no significant mortality.

Also, the recombinant clone expressing the Cry2Af protein shows a significant mortality when tested on selected Lepidopteran insects.

Also, an analysis was done to determine the LC50 and LC90 values for the recombinantly produced Cry2Ae protein, in comparison with the known Cry2Aa and Cry2Ab proteins.

For this assay, insect-specific artificial diet was dispensed in wells of Costar 24-well plates. 50 microliter of alkaline (pH12) extract of spore-crystal mixtures of the recombinant Bt strain containing the cry2Ae gene originating from XL1Blue:pUC1099Eclone7, was applied on the surface of the diet and dried in a laminar air flow. The diet for *S. frugiperda* en *O. nubilalis* contained: 1000 ml water; agar: 20 g; cornflour: 112 g; wheat germ: 28 g; yeast: 30 g; ascorbic acid: 4.8 g; benzoic acid: 1.2 g; nipagin: 1 g; aureomycin: 0.06 g; nystatin: 0.03 g. The diet for *H. virescens* en *H. zea* contained: 1000 ml water; agar: 20 g; soyflour: 81 g; wheat germ: 36 g, sucrose: 14.7 g; corn oil: 5 ml; Wesson salt mixture: 10 g; Vanderzant vitamin mixture: 9.5 g; sorbic acid: 1.1 g; nipagin: 1 g; aureomycin: 0.34 g; nystatin: 0.06 g. Different protein concentrations were tested so that an LC50 value could be determined. For tests on *H. zea*, *H. virescens* and *S. frugiperda*, one larva was placed in each well and 20 larvae were used per sample. For tests on *O. nubilalis*, two larva were placed in each well and 24 larvae were used per sample. Dead and living larvae were counted on the seventh day (on the sixth day for *S. frugiperda*, on the fifth day for *O. nubilalis*). The LC50 and LC90 values were calculated with probit analysis (POLO program, LeOra Software, 1987, POLO-PC. A user's guide to probit or logic analysis. Berkeley, Calif.). The results are shown in Table III below.

TABLE III

| Toxin | Conc. | LC50(LC90) values, both in ng/cm² | | | |
|---|---|---|---|---|---|
| | | Sf | Hz | Hv | On |
| Cry2Ae | 1160 (*1930) | 1154 (3708) | 62 (655) | 10 (20) | *188 (*1383) |
| Cry2Aa | 2910 (*470) | 2906 (10945) | 1921 (7740) | 35 (138) | *294 (*2854) |
| Cry2Ab | 1290 | 1498 (8150) | 448 (2152) | 82 (248) | NT |

NT: not tested; Conc.: total protein concentration in alkaline extract of recombinant Bt strain producing the relevant protein in microgr/ml; an asterisk denotes that the result for *O. nubilalis* was obtained with a different batch having a different protein concentration (indicated between brackets under the column "Conc."); controls (normal diet, added PBS-BSA or crystal-minus control Bt strain) give no more then 0-5% mortality.

Using the same experimental setup as above for *Ostrinia nubilalis*, but using purified Cry2Ae protein against the velvetbean caterpillar, *Anticarsia gemmatalis*, (testing 20 wells with 1 larva per concentration) a high activity of this protein against this important soybean pest insect was found. The $LC_{50}$ value for the purified Cry2Ae protein to this insect was found to be 0.44 ng/cm² (at 95% confidence level; this $LC_{50}$ value is the mean value of 2 assays of different bio-batches of purified protein), the $LC_{90}$ value was found to be 7.79 ng/cm² (at the 95% confidence level; this $LC_{90}$ value is the mean value of 2 bio-assays of different to batches of purified protein). Using the same experimental setup as above for *Ostrinia* with purified Cry2Ae protein, the significant toxicity of this protein to *Helicoverpa Zea* and *Ostrinia Nubilalis* was confirmed ($LC_{50}$ values to these insects were found to be 145.1 and 48.31 ng/cm², respectively (at 95% confidence level, these $LC_{50}$ values are the mean values of 2 bio-assays of different batches of purified protein on each respective insect)).

These results show that the new Cry proteins of the invention, and particularly the Cry2Ae protein, are useful proteins with high activity to relevant Lepidopteran insect pests, particularly to *Heliolhis zea, Ostrinia nubilalis, Anticarsia gemmatalis*, and *Helicoverpa zea* which are commercially damaging insect pests for plants such as soybean, cotton and corn.

The sequences determined for the isolated cry2A genes of the invention, and the determined amino acid sequence, are shown in the enclosed Sequence Listing. Pairwise alignments using the GAP program in the Wisconsin package of GCG indicated the levels of sequence identity with other Cry2A sequences (for the sequences of the known Cry2A proteins and DNAs, see Crickmore et al. (1998) and the above recited internet website), as shown in Table IVA and IVB (GCG defaults were used within the GAP program; for the amino acid sequence comparisons, the blosum62 scoring matrix was used, for the DNA sequence comparisons, the nwsgapdna scoring matrix was used).

TABLE IV.A

Percentage sequence identity at the protein level:

| | Cry2Ae1 | Cry2Af1 | Cry2Ag1 |
|---|---|---|---|
| Cry2Aa1 | 90.837 | 88.942 | 78.905 |
| Cry2Ab1 | 89.889 | 94.471 | 77.331 |
| Cry2Ac1 | 80.547 | 80.386 | 79.869 |
| Cry2Ad1 | 87.362 | 91.943 | 76.849 |
| Cry2Ae1 | | 93.365 | 79.871 |
| Cry2Af1 | | | 79.549 |

TABLE IV.B

Percentage sequence identity at the DNA level:

| | cry2Ae1 | cry2Af1 | cry2Ag1 |
|---|---|---|---|
| cry2Aa1 | 91.206 | 89.995 | 81.994 |
| cry2Ab1 | 91.890 | 94.839 | 81.404 |
| cry2Ac1 | 84.298 | 85.209 | 84.041 |
| cry2Ad1 | 90.627 | 93.470 | 81.136 |
| cry2Ae1 | | 94.576 | 81.589 |
| cry2Af1 | | | 82.233 |

Example 4

Production of the Novel Cry Proteins in Transformed Plants

Chimeric genes each encoding the Cry2Ae, Cry2Af and Cry2Ag proteins are made using well known procedures, using promoters such as the CaMV 355 (Hull and Howell, 1987) and ubiquitin (Christensen et al., 1992) promoters. Preferably, the codon usage of the open reading frame is adapted to that of the host plant so as to optimize expression efficiency, as described in published PCT patent application WO 94/12264. Also, in some chimeric genes DNA sequences encoding a transit peptide (as described in the description) are included to target the Cry2A protein of the invention to the plant chloroplasts.

For transformation of corn and cotton with a chimeric gene encoding the Cry2Ae protein, several chimeric gene constructs were inserted in *Agrobacterium* strain plasmids. These constructs included: constructs pACS9 and pACS11 wherein the cry2Ae coding sequence of SEQ ID No. 7 was functionally linked to the 3552 promoter from Cauliflower Mosaic Virus (Odell et al., 1985), a leader sequence from the chlorophyll a/b binding protein gene from Petunia (Harpster et al., 1988), and a 3' transcript termination and polyadenylation region of the 35S gene from Cauliflower Mosaic Virus (Sanfacon et al, 1991), and constructs pACS12 and pACS13 with the same regulatory regions and the same cry2Ae coding region, except that also a DNA sequence encoding the TpssuAt transit peptide allowing chloroplast targeting (Krebbers et al., 1988) was inserted at the 5' end of the cry2Ae coding region, so that a transit peptide fusion protein is produced. These constructs also included either a DNA sequence encoding a glyphosate herbicide resistance protein (described in published PCT patent application WO 97/04103, linked to an optimized transit peptide (U.S. Pat. No. 5,635,618)) or a DNA sequence encoding a glufosinate herbicide resistance protein (Thompson et al., 1987) as selectable marker under the control of the CsVMV promoter of the Cassava Vein Mosaic Virus (Verdaguer et al., 1996, 1998) and the 3' transcript termination and polyadenylation region of the nopaline synthase gene (Depicker et al., 1982). Corn cells were stably transformed with the pACS9, pACS11, pACS12 and pACS13 constructs by either *Agrobacterium*-mediated transformation as described in U.S. Pat. No. 6,140,553, incorporated by reference. Cotton cells were stably transformed with the pACS 9, pACS11, pACS12 and pACS13 constructs using the transformation method described in PCT patent publication WO 00/71733, incorporated herein by reference. Rice cells are stably transformed with the method described in published PCT patent application WO 92/09696. Tobacco cells were stably transformed with the pACS11 and pACS12 constructs using *Agrobacterium*-mediated transformation, essentially as described in EP patent 0 116 718 or Deblaere et al. (1987).

The transformed cells and plantlets regenerated therefrom are grown in media containing the selective agents phosphinothricin or glyphosate, so that most if not all of the regenerated plants will be transformed.

Regenerated transformed tobacco, corn, cotton and rice plants are selected by Cry2A ELISA, Northern and Southern blot and according to insecticidal efficacy and agronomic characteristics. Chimeric cry2A gene-containing progeny plants show improved resistance to insects compared to untransformed control plants with an appropriate segregation of the insect resistance and the transformed phenotype. Protein and RNA measurements show that plants with increased insect resistance have a higher expression of the novel Cry2A protein in their cells.

REFERENCES CITED

Adang et al. (1985). Gene 36, 289.
An et al. (1996). Plant J. 10, 107.
Bennetzen & Hall. (1982). J. Biol. Chem. 257, 3026-3031.
Berhard, K. and Utz, R., "Production of *Bacillus thuringiensis* insecticides for experimental and commercial uses", In *Bacillus thuringiensis, An Environmental Biopesticide: Theory and Practice,* 0.255-267, eds. Entwistle, P. F., Cory, J. S.,
Bailey, M. J. and Higgs, S., John Wiley and Sons, New York (1993).
Bih et al. (1999), J. Biol. Chem. 274, 22884-22894.
Choi et al., GenBank accession number AF200816 (1999).
Christensen et al. (1992) Plant mol. Biol. 18, 675-689.
Christou et al. (1990). Trends Biotechnology 8, 145.
Cordera et al. (1994) The Plant Journal 6, 141.
Cornejo at al. (1993) Plant Mol. Biol. 23, 567-581.
Cornelissen et al. (1986) EMBO J. 5, 37-40.
Crickmore et al. (1998) Microbiol. Mol. Biol. Rev. 62(3), 807-13.
Datta et al., Bio/Technology 8, 736-740 (1990).
Deblaere et al. (1987) Methods in Enzymology 153, 277-292.
De Pater et al., 1992, Plant J. 2, 834-844.
Depicker et al., 1982, J. Molec. Appl. Genetics 1, 561-573.
Dulmage, H. T., "Production of Bacteria for Biological Control of Insects" in Biological Control in Crop Production, Ed. Paparizas, D. C., Osmun Publishers, Totowa, N. J., USA, pp. 129-141 (1981).
English et al., Insect Biochem. Molec. Biol. 24, 1025-1035 (1994).
Estruch et al., (1996), Proc Natl Acad Sci USA 93, 5389-94.
Franck et al., Cell 21, 285-294 (1980)
French at al., Anal. Biochem. 156, 417-423 (1986).
Ffrench-Constant and Bowen (2000) Cell Mol Life Sci 57, 828-33.
Fromm et al., Bio/Technology 8, 833-839 (1990).
Gardner et al., Nucleic Acids Research 9, 2871-2887 (1981)
Ge et al., J. Biol. Chem. 266, 17954-17958 (1991)
Gielen et al., EMBO J. 3, 835-845 (1984).
Gordon-Kamm et al., The Plant Cell 2, 603-618 (1990).
Gould et al., Plant Physiol. 95, 426-434 (1991).
Harpster et al., (1988), Molecular and General Genetics 212, 182-190.
Hesse et al. (1989), EMBO J. 8 2453-2461.
Hinchee et al. (1988) Bio/Technology 6, 915.
Ho et al. (1989). Gene 77, 51-59.
Höfte et al., Appl. and Environm. Microbiol. 54, 2010-2017 (1988).
Höfte and Whiteley, Microbiological Review 53, 242-255 (1989).
Hull and Howell, Virology 86, 482-493 (1987)
Itakura et al. (1977). Science 198, 1056-1063.
Jansens et al. (1997) Crop Science 37, 1616-1624.
Keil et al. (1986), Nucl. Acids Res. 14, 5641-5650.
Klösgen et al. (1989), Mol. Gen. Genet. 217, 155-161.
Klösgen and Well (1991), Mol. Gen. Genet. 225, 297-304.
Kota et al. (1999) Proc. Natl. Acad. Sci. USA 96, 1840-1845.
Krebbers et al. (1988) Plant Molec. Biol. 11, 745-759.
Last et al. (1990) Theor. Appl. Genet. 81, 581-588.
Lereclus et al., Bio/Technology 10, 418 (1992).
Mahillon et al, FEMS Microbial. Letters 60, 205-210 (1989).
Maxam and Gilbert, Methods in Enzymol. 65, 499-560 (1980).
McBride et al., 1995, Bio/Technology 13, 362
Morris et al. (1999), Biochem. Biophys. Res. Commun. 255, 328-333.
Murray et al., M., Nucleic Acids Research 17(2), 477-498 (1989).
Neuhaus & Rogers (1998), Plant Mol. Biol. 38, 127-144.
Odell et al. (1985) Nature 313, 810-812.

Oelmuller et al., Mol. Gen. Genet. 237, 261-272 (1993).
Park et al. (1997), J. Biol. Chem. 272, 6876-6881.
Sanfacon et al. (1991), Genes and Development 5, 141-149.
Sanger et al., Proc. Natl. Acad. Sci. USA. 74(12), 5463-5467 (1977).
Schnepf et al. (1985). Journal of Biological Chemistry 260, 6264.
Schnepf et al. (1998). Microbial. Mol. Biol. Rev. 62(3), 775-806.
Shcherban et al. (1995), Proc. Natl. Acad. Sci. USA 92, 9245-9249.
Shimamoto et al., Nature 338, 274-276 (1989).
Stanssens et al, Nucleic Acids Research 12, 4441-4454 (1989).
Sutliff et al. (1991) Plant Molec. Biol. 16, 579-591.
Tavladoraki et al. (1998), FEBS Lett. 426, 62-66.
Terashima et al. (1999), Appl. Microbiol. Biotechnol. 52, 516-523.
Thompson et al. (1987), EMBO J. 6, 2519-2523.
Vaeck at al., 1987, Nature 328, 33-37.
Van Den Broeck et al., 1985, Nature 313, 358.
Vanderzant, J. Econ. Entomol. 55, p. 140 (1962).
Van Rie et al., Science 247, 72 (1990).
Velten at al., J., EMBO J. 3, 2723-2730 (1984).
Velten and Schell, Nucleic Acids Research 13, 6981-6998 (1985)
Verdaguer et al., Plant Mol. Biol. 31, 1129-1139 (1996).
Verdaguer eta, Plant Mol. Biol. 37, 1055-1067 (1998).
Visser at al., "Domain-Structure Studies of *Bacillus thuringiensis* Crystal Proteins: A Genetic Approach", In *Bacillus thuringiensis*, An Environmental Biopesticide: Theory and Practice, pp. 71-88, eds. Entwistle, P. F., Cory, J. S., Bailey, M. J. and Higgs, S., John Wiley and Sons, New York (1993).
Wada et al. (1990). Nucl. Acids Res. 18, 2367-1411.
Waterfield et al. (2001) Trends Microbiol 9, 185-91.
White et al. (1989). Trends in Genet. 5, 185-189.
Wong et al. (1992), Plant Molec. Biol. 20, 81-93.
Zhang at al. (1991) The Plant Cell 3, 1155-1165.

The invention claimed is:

1. An isolated nucleic acid sequence encoding an insecticidal protein comprising the amino acid sequence of SEQ ID No. 4, an insecticidal portion thereof, or an insecticidal protein having at least 97% sequence identity thereto.

2. The nucleic acid sequence of claim 1, said nucleic acid sequence encoding an insecticidal protein comprising the amino acid sequence of SEQ ID No. 4 from an amino acid position between amino acid position 1 and 51 to an amino acid position between amino acid position 624 and 632 in SEQ ID No. 4.

3. The nucleic acid sequence of claim 1, said nucleic acid sequence encoding an insecticidal protein comprising the amino acid sequence from an amino acid position between amino acid position 1 and 51 to amino acid position 632 in SEQ ID No. 4.

4. The nucleic acid sequence of claim 1, said nucleic acid sequence encoding an insecticidal protein comprising the amino acid sequence from amino acid position 1 to an amino acid position between amino acid positions 624 and 632 in SEQ ID No. 4.

5. The nucleic acid sequence of claim 1, said nucleic acid sequence encoding an insecticidal protein comprising the amino acid sequence of SEQ ID No. 4.

6. The nucleic acid sequence of claim 1, wherein said nucleic acid sequence is DNA.

7. The nucleic acid sequence of claim 1, wherein said nucleic acid sequence comprises an artificial DNA sequence having a different codon usage compared to SEQ ID NO: 3 but encoding the same protein or its insecticidal portion.

8. The nucleic acid sequence of claim 1, wherein said nucleic acid sequence comprises the nucleotide sequence of SEQ ID No. 3.

9. The nucleic acid sequence of claim 1, wherein the encoded protein starts with a Met-Asp or Met-Ala dipeptide for optimal translation initiation.

10. A chimeric gene comprising the nucleic acid of claim 1, wherein said chimeric gene is under the control of a plant-expressible promoter.

11. The chimeric gene of claim 10, further comprising a DNA sequence encoding a targeting or transit peptide for targeting to a vacuole, mitochondrium, chloroplast, plastid, or for secretion.

12. The chimeric gene of claim 11, wherein said DNA sequence encodes a chloroplast transit peptide.

13. A chimeric gene comprising the following operably-linked elements:
 a) a 35S promoter derived from Cauliflower Mosaic Virus;
 b) the nucleic acid sequence of claim 1; and
 c) a 3' transcript termination and polyadenylation region of a 35S gene from Cauliflower Mosaic Virus.

14. The chimeric gene of claim 13, wherein said chimeric gene further comprises a DNA sequence encoding a TpssuAt transit peptide, said TpssuAt transit peptide inserted at the 5' end of the coding sequence.

15. A transformed plant cell, plant or seed comprising the chimeric gene of claim 10.

16. The plant cell, plant or seed of claim 15, wherein said plant cell, plant or seed is corn, cotton, rice, tobacco, oilseed rape, Brassica species, eggplant, soybean, potato, sunflower, tomato, sugarcane, tea, beans, tobacco, strawberry, clover, cucumber, watermelon, pepper, oat, barley, wheat, dahlia, gladiolus, chrysanthemum, sugarbeet, sorghum, alfalfa, or peanut.

17. A transformed micro-organism comprising the nucleic acid sequence of claim 1.

18. A process for producing an insect resistant plant comprising transforming plant cells with the chimeric gene of claim 10, and regenerating transformed plants from said plant cells that are resistant to insects.

19. The process of claim 18, wherein said insect is *Heliothis virescens, Helicoveipa zea, Helicoveipa armigera, Anticarsia gemmatalis, Ostrinia nubilalis, Chilo suppressalis, Chilo partellus, Scirpophaga incertulas, Sesamia inferens, Cnaphalocrocis medinalis, Marasmia patnalis, Marasmia exigua, Marasmia ruralis*, or *Scirpophaga innotata*.

20. A plant, plant cell or seed comprising the chimeric gene of claim 10, and a second chimeric gene comprising a DNA sequence encoding an insecticidal Cry1F protein or a toxic fragment thereof, a hybrid protein derived from a Cry1F protein, a Cry1A-Cry1F hybrid protein, a Cry1A-type protein or a toxic fragment thereof, a Cry1Ac protein or a Cry1Ab-Cry1Ac hybrid protein, or a VIP3Aa protein or a toxic fragment thereof.

21. A transgenic cotton plant comprising the nucleic acid sequence of claim 1, and a DNA sequence encoding an insecticidal Cry1Ac or VIP3Aa protein.

22. A transgenic plant comprising a DNA encoding the chimeric gene of claim 10, and a DNA sequence encoding a protein conferring tolerance to a herbicide based on glufosinate or glyphosate.

23. The nucleic acid sequence of claim 1, wherein said insecticidal protein comprises the amino acid sequence of SEQ ID No. 4, wherein 5 to 10 amino acids are added, replaced or deleted without significantly changing the insecticidal activity of said protein.

24. The nucleic acid sequence of claim 1, wherein said insecticidal protein comprises the amino acid sequence of SEQ ID No. 4, wherein less than 5 amino acids are added, replaced or deleted without significantly changing the insecticidal activity of said protein.

25. An isolated nucleic acid sequence encoding a protein comprising the amino acid sequence of SEQ ID No. 4, or a protein having at least 97% sequence identity thereto.

26. A chimeric gene comprising the nucleic acid of claim 5, wherein said chimeric gene is under the control of a plant-expressible promoter.

27. A chimeric gene comprising the nucleic acid of claim 25, wherein said chimeric gene is under the control of a plant-expressible promoter.

* * * * *